United States Patent
Mann et al.

(10) Patent No.: US 6,618,622 B1
(45) Date of Patent: Sep. 9, 2003

(54) METHOD AND APPARATUS OF DETERMINING ATRIAL CAPTURE THRESHOLD WHILE AVOIDING PACEMAKER MEDIATED TACHYCARDIA

(75) Inventors: Brian M. Mann, Beverly Hills, CA (US); Melinda Endaya, Granada Hills, CA (US); Paul A. Levine, Santa Clarita, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/851,715

(22) Filed: May 8, 2001

Related U.S. Application Data

(63) Continuation of application No. 09/395,640, filed on Sep. 14, 1999, now Pat. No. 6,259,950, and a continuation-in-part of application No. 09/201,102, filed on Nov. 30, 1998, now abandoned, and a continuation-in-part of application No. 08/855,548, filed on May 13, 1997, now Pat. No. 5,891,178.

(60) Provisional application No. 60/017,671, filed on May 14, 1996.

(51) Int. Cl.[7] ............................................. A61N 1/362
(52) U.S. Cl. ............................................. 607/28; 607/14
(58) Field of Search .............................. 607/28, 14, 9, 607/27

(56) References Cited

U.S. PATENT DOCUMENTS 5,374,280 A * 12/1994 den Dulk ..................... 607/14
6,246,906 B1 * 6/2001 Hsu et al. ..................... 607/4

* cited by examiner

Primary Examiner—Kennedy Schaetzle

(57) ABSTRACT

A pacemaker programmer and diagnostic system retrieves information stored within a pacemaker and analyzes the retrieved data in real time. The stored information can be retrieved by means of a telemetry communication link. The pacemaker automatically lengthens an AV delay. The pacemaker determines atrial capture by generating atrial stimulation pulses while maintaining the ventricular stimulation pulse amplitude at a level known to ensure ventricular capture, and by detecting loss of atrial capture. In response to the loss of atrial capture, a processor automatically records the atrial capture threshold, and restores the AV delay to its pre-test value. The pulse generator also delivers a backup atrial stimulation pulse concurrent with a ventricular stimulation pulse to reduce the possibility of a retrograde P-wave initiating a pacemaker-mediated tachycardia (PMT).

8 Claims, 26 Drawing Sheets

METHOD AND APPARATUS OF DETERMINING ATRIAL CAPTURE THRESHOLD WHILE AVOIDING PACEMAKER MEDIATED TACHYCARDIA

PRIORITY CLAIM

This application is a continuation of U.S. application Ser. No. 09/395,640, filed Sep. 14, 1999, now issued as U.S. Pat. No. 6,259,950, and is a continuation-in-part application of U.S. application Ser. No. 09/201,102, filed Nov. 30, 1998, now abandoned, and is a continuation-in-part of U.S. application Ser. No. 08/855,548, filed May 13, 1997, now issued as U.S. Pat. No. 5,891,178, which, in turn, claims the benefit of U.S. Provisional Application Ser. No. 60/017,671, filed May 14, 1996, all of which are incorporated herein by reference in their entirety.

FIELD OF THE INVENTION

The present invention relates generally to cardiac pacemakers, and other types of implantable medical devices, which can be programmed and/or analyzed following implantation using an external diagnostic/programmer system. More particularly, the invention relates to an implantable dual-chamber pacemaker, including software routines thereof, for automatically determining atrial capture using backup atrial stimulation to prevent pacemaker-mediated tachycardia.

BACKGROUND OF THE INVENTION

Implantable cardiac pacemakers commonly store a variety of different types of diagnostic data which assist the physician in evaluating both the operation of the patient's heart and the operation of the implanted device. Depending upon the particular pacemaker and its mode of operation, this information may include, for example, a heart rate histogram (which indicates the distribution of the patient's heart rate over a period of time, such as one month), an event histogram (which indicates the distribution of the various sensing and stimulation events), a sensor indicated rate histogram (which indicates the distribution over time of the recommended pacing rate indicated by an implanted sensor), a variety of event counters, one or more event-triggered intracardiac electrograms, and the status of the pacemaker's battery.

The various items of diagnostic data may be retrieved from the pacemaker for display and evaluation using a pacemaker programmer/diagnostic system ("programmer"), which uses RF telemetry to communicate with the implanted device. This is typically accomplished during routine follow-up visits of the patient to the clinic, during which time the patient is asked to hold a telemetry wand in the locality of the implanted pacemaker. To read out and view a particular item of information (e.g., a heart rate histogram), the physician employs a user interface of the programmer to designate the diagnostic item to be retrieved, and then initiates the retrieval. The programmer in-turn interrogates the pacemaker to cause the pacemaker to transmit the selected diagnostic item, and then receives and displays the selected item on the screen. The physician may also initiate various types of tests using the programmer, such as a ventricular or atrial capture test which determines the minimum pulse voltage needed to effectively stimulate the respective chamber of the heart. The physician may retrieve and adjust various programmable pacing parameters, such as sensor control parameters that are used to adjust the pacing rate according to the output of an event (or other) sensor which senses electrical activity generated within the cardiac tissue.

During the follow-up visit, it is common for the physician (or other clinician) to follow a predetermined sequence or "protocol" for the evaluation of the patient. The particular protocol will often vary from physician-to-physician and/or clinic-to-clinic, and may depend upon the medical condition of the patient. By way of example, a follow-up protocol may include the steps of:

(1) retrieving, viewing and printing the atrial and ventricular rate histograms;
(2) retrieving and viewing (and optionally printing) the event histogram;
(3) conducting ventricular and atrial sense tests;
(4) conducting ventricular and atrial capture tests; (5) contingent upon the results of steps 1–4, retrieving and viewing the R-wave and P-wave histograms (indicative of the contraction of the ventricles and the atria, respectively);
(6) retrieving, viewing and printing the sensor indicated rate histogram; and
(7) if appropriate, adjusting the sensor control parameters. During each step of the protocol, the physician typically interviews the patient and records the patient's comments. At the end of the examination, the physician normally prepares a written report, which typically includes various printouts of the retrieved diagnostic data.

One problem with current diagnostic methods used to evaluate the follow-up patient is that the physician is typically required to scroll through large volumes of data on the programmer screen, even though only selected portions of this data are significant for diagnostic purposes. This is true, for example, in the case of atrial and ventricular capture tests, in which the physician is typically presented with a snap-shot of real-time data (typically, several seconds long), and must scroll through the data to locate the point at which capture was lost. Because much of the data viewed by the physician is insignificant, the process tends to be inefficient.

Based upon the results of the pacemaker diagnostic, the physician sometimes alters the pacemaker parameters (i.e., the stored valves that specify the therapy delivered by the pacemaker). These modifications to the pacemaker parameters are typically standard given a certain set of results. However, the steps of programming each parameter change tend to be time consuming, further adding to the overall time required to complete the follow-up examination.

Many conventional pacemaker diagnostic systems merely provide historical data to the physician and are not capable of providing for real-time analysis of pacemaker parameters. Even those systems which do provide real-time analysis of some diagnostic items do not allow the clinician to modify pacemaker parameters "on the fly" so that the clinician can immediately observe the results of such parameter modification. This can significantly reduce the physician's ability to actively interact with the pacemaker to achieve an unambiguous result.

SUMMARY OF THE INVENTION

The present invention addresses these and other concerns by providing an improved programmer. According to one preferred embodiment, the improved programmer can automatically step through a pacemaker test sequence and automatically identify significant events or transitions (e.g., the loss of atrial or ventricular capture, substantial heart rate changes, etc.). This aspect of the invention greatly reduces the amount of time it takes a physician to evaluate pacemaker performance, since it reduces or eliminates the need for the physician to manually scroll through the test sequence.

According to another aspect of the invention, the programmer of a preferred embodiment automatically suggests pacemaker parameter modifications based upon (i) the results of the automatic analysis and (ii) patient history trends stored within the pacemaker. In order to effect a modification in a parameter, the suggested modification is presented to the physician for confirmation. This makes parameter modification essentially a "one step" process.

According to yet another aspect of the invention, the programmer evaluates the pacemaker operations in real time. The evaluation of pacemaker operation on a real-time basis allows the physician to interactively modify parameters "on the fly" and evaluate the results immediately. This in turn allows the physician to test and program the pacemaker more rapidly, and to achieve an unambiguous result. In addition, real-time analysis and interaction with the telemetry system minimizes pauses, and prevents unwanted rhythms (e.g., retrograde conduction and PMT).

According to a preferred embodiment, the programmer retrieves information stored within the pacemaker and analyzes the retrieved data in real time. The stored information can be retrieved by means of a telemetry communication link.

The pacemaker automatically lengthens an AV delay. The pacemaker determines atrial capture by generating atrial stimulation pulses while maintaining the ventricular stimulation pulse amplitude at a level known to ensure ventricular capture, and by detecting loss of atrial capture.

In response to loss of atrial capture, a processor automatically records the atrial capture threshold, and restores the AV delay to its pre-test value. The pulse generator also delivers a backup atrial stimulation pulse concurrent with a ventricular stimulation pulse to reduce the possibility of a retrograde P-wave initiating a pacemaker-mediated tachycardia (PMT).

According to another embodiment, the pacemaker lengthens a post-ventricular atrial refractory period (PVARP) prior to detecting loss of atrial capture. In response to the detection of loss of atrial capture, the processor restores the PVARP to its pre-test value.

BRIEF DESCRIPTION OF THE DRAWINGS

These and other features and advantages of the invention will now be described with reference to the drawings of a preferred embodiment, which is intended to illustrate and not to limit the invention, and in which.

DETAILED DESCRIPTION OF THE PREFERRED EMBODIMENTS

Figure 1:
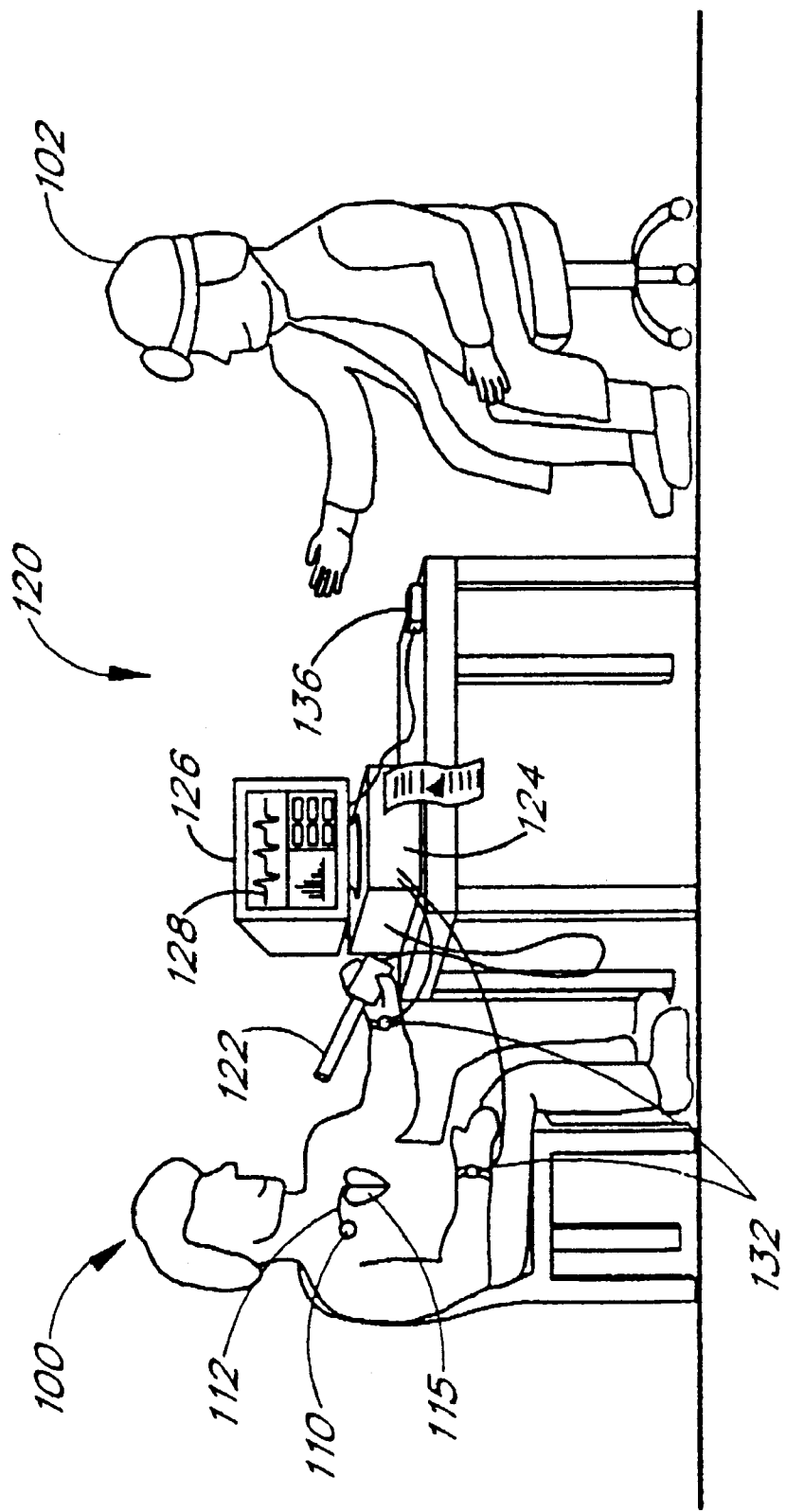
FIG. 1 illustrates a patient in the context of a follow-up session with a clinician using a programmer system in accordance with the invention.

A preferred embodiment of the present invention is an interactive pacemaker programmer system that includes various software-based features which allow a physician to program and evaluate the operation of an implanted pacemaker with increased accuracy and efficiency. In accordance with one aspect of the invention, the programmer automatically and temporarily changes various program parameters while collecting diagnostic data indicative of the effectiveness of such parameter changes. The data collected includes, among other items, ECG data, intracardiac electrogram (IEGM)data, and markers. As is well known in the art, an ECG is a graphic depiction of the electrical signal emitted by active cardiac tissue and recorded through electrodes placed on the surface of the body. Similarly, an IEGM is a graphic depiction of the electrical signal emitted by active cardiac tissue and recorded through electrodes placed on or within the heart. This graphical depiction is sometimes referred to as an electrogram. As used herein, an event marker, or a marker, is a real-time annotation of paced and sensed events for a pacemaker, usually displayed on a display screen in conjunction with the simultaneously recorded surface ECG.

In accordance with a further aspect of the invention, novel use of historical data is made in order to automatically perform trend analysis. That is, multiple events are recorded and stored within the pacemaker in the form of, for example, an event histogram, and a statistical analysis is performed on this historical data (preferably within the programmer) in order to make decisions for setting the pacemaker parameters. These decisions are based upon trends observed within the historical data.

A preferred embodiment of the present invention also allows analysis to be performed even in the presence of IEGM signal amplifier saturation after the pacing spike. As is well known in the art, the pacing spike typically drives the sensing amplifier for the intracardiac electrogram into saturation, since the pacing pulse has a relatively high amplitude compared to the natural electrical signals generated within the cardiac tissue. As a result, prior systems are not able to perform analysis in the presence of IEGM signal amplifier saturation. In accordance with the invention, however, this difficulty is avoided by using tests which use data surrounding the pacing spike. These tests use surface ECG waveforms and markers to determine results, in place of IEGM signal.

In accordance with a further aspect of the present invention, the removal of the repolarization artifact, which is often quite difficult, is not required. Repolarization is the recovery process of excitable tissue following depolarization. Thus, repolarization involves the voltage potential of the cardiac tissue returning to its resting value. For example, ventricular polarization is represented on the ECG by the T-wave, while atrial repolarization is usually not visible on the ECG, since it is obscured by the simultaneously occurring QRS complex. This repolarization process sometimes produces artifacts which inhibit an accurate sensing of the QRS complex so that it is desirable to remove the repolarization artifact. A preferred embodiment of the present invention analyzes the ECG waveform in relation to surrounding marker events, and therefore does not require the removal of repolarization artifact. The markers provide a "time tag" so criteria for detecting the corresponding event in the ECG waveform can be less stringent than in a morphological analysis.

Automatic testing of pacing and sensing safety margins are incorporated into a preferred embodiment in order to provide, in addition to the qualitative assessments of conventional systems, a quantitative assessment of pacing and sensitivity adequacy. Because the system of the present invention analyzes the data in real-time and interacts with the telemetry system, it is capable of minimizing pauses and preventing unwanted rhythms (e.g., retrograde conduction and PMT) which can result from either manual capture testing or automatic capture testing with a delayed analysis and/or a passive system. For example, because retrograde conduction is a backward conveyance of the electrical impulse originating in the junction or ventricles and traveling backward to the atria, causing an atrial depolarization, such an abnormal conduction is undesirable. Retrograde conduction can be seen on the ECG by P-waves of opposite polarity to sinus P-waves and usually follows an ectopic or ventricular paced event. Thus, when an analysis is performed in real-time, it is possible to mitigate the effects of retrograde conduction by one of two ways. If the retrograde conduction is being caused by ventricular paced events, the AV delay may be shortened so the ventricular pulse is delivered (and the retrograde impulse is conducted) while the atrial tissue is still refractory. In cases where the atrium does depolarize, the PVARP is increased so the pacemaker "ignores" the retrograde P-wave.

Similarly, pacemaker-mediated tachycardia (PMT) is a cardiac arrhythmia characterized by a rapid rate induced by competition between the paced and native rhythms and sustained by the continued participation of the pacemaker. Thus, if an analysis is performed in real-time, PMT can be avoided, since the monitoring physician is able to immediately discontinue the pacemaker-induced rhythm so that only the natural rhythm causes the heart to beat.

An overview of the programmer and the follow-up process will now be provided with reference to FIGS. 1–6. The above features of the programmer will then be described in greater detail with reference to FIGS. 7–20.

1. Overview (FIG. 1)

FIG. 1 is a diagram of a patient 100 in the context of a hypothetical follow-up session with a clinician 102, and will be used to provide an overview of the follow-up examination process. The patient has an implanted, battery-powered pacemaker 110, such as an AFFINITY® pacemaker available from PACESETTER, Inc., 15900 Valley View Court, Sylmar, Calif. One or more pacing leads 112 extend from the pacemaker 110 into the patient's heart 115. The pacing leads 112 are used to apply electrical pulses to the inner tissue of the heart (typically within the right ventricle and/or the right atrium), and may also be used to sense intrinsic electrical activity within the heart. The pacemaker 110 and/or the leads 112 may also carry one or more sensors (not shown), such as an activity sensor for sensing changes in the patient's level of physical activity.

The pacemaker 110 includes a conventional or available telemetry circuitry (not shown) which permits the exchange of information with an external "APS® III" programmer 120 via a conventional or available telemetry wand 122. The pacemaker 110 includes various programmable parameters, including but not limited to an AV delay, ventricular sensitivity, atrial sensitivity, post-ventricular refractory period (PVARP).

In a preferred embodiment, the programmer 120 includes a processor (a microprocessor, or a central processing unit CPU) such as a 486 or Pentium® based computer system 124, and includes a monitor 126 having a touch-sensitive display screen 128. (In one implementation, the display screen 128 and computer system 124 are integrated within a common housing.) The computer system 124 may be provided with an internal printer, as depicted in FIG. 1, and/or may be connected to an external printer (not shown).

During the follow-up session, the patient 100 is asked to hold the telemetry wand 122 near the implanted pacemaker 110 to permit the interrogation of the pacemaker 110, which involves the transmission of RF commands to the pacemaker 110. Data transfers between the programmer 120 and the pacemaker 110 are accomplished using a standard interrogation protocol, in which the programmer 120 transmits commands (via the telemetry wand 122) to the pacemaker 110 to cause the pacemaker to take specific actions, such as transmit a particular record of diagnostic data.

In addition to the data collected from the pacemaker 110, the programmer receives surface electrocardiograph (ECG) signals from conventional or available surface electrodes 132, which attach to the skin of the patient 100. The ECG signals are displayed to the clinician 102 on a continuous, real-time basis via the monitor 126, and are used by the programmer 120 to perform tests relating to, for example, atrial and ventricular capture.

The pacemaker 110 stores a variety of different diagnostic data records, including various types of histograms, real-time event records, event counters, and event-triggered snapshots of data. These diagnostic data records are collected by the pacemaker 110 over a period of time, such as between visits of the patient to the clinic, and can be retrieved and displayed to allow the clinician to evaluate the effectiveness of the pacing treatment. The stored diagnostic data records may also include information relating to the operation of the pacemaker itself, such as a history of the pacemaker's battery voltage. Accordingly, as used herein, the term "diagnostic data record," or simply "diagnostic record," refers to a collection of data captured or generated by the implanted device over a period of time, which may be retrieved from the implanted device to obtain information about the patient and/or the operation of the implanted device.) The particular diagnostic data records stored by the pacemaker 110 depend upon both the model of the pacemaker and its programmed mode of operation.

Also, the pacemaker 110 stores a variety of parameters (referred to generally as "parametric data") which define the therapy administered by the pacemaker 110, and which can be modified during the follow-up session. These parameters typically include, for example the base rate (i.e., the rate at which pulses are applied to the heart in the absence of intrinsic activity), the AV delay (i.e., the delay between a sensed or paced atrial event and the delivery of a ventricular output pulse), the amplitude and width of pulses applied to the atrium and/or ventricle, and various sensor parameters for defining the control relationship between sensor output and pacing rate. As with the diagnostic data records, the specific program parameters which may be modified depend upon both the model of the pacemaker and its mode of operation. Typically, the parameters are retrieved from the pacemaker one set at-a-time (such as the set of all sensor parameters), as opposed to being retrieved on a parameter-specific basis.

In the course of a typical follow-up session the clinician uses either a conventional or available programmer, or the programmer 120 of the present invention, to retrieve, view and print various diagnostic data records, and to clear stored diagnostic data records from memory, to permit the subsequent capture of new diagnostic data. The clinician may also retrieve and view the various sets of parameters, as well as information about the pacemaker and the patient. In addition, the clinician may use the programmer to initiate various diagnostic tests, such as an atrial capture test or a retrograde conduction test. Based on the test results and the clinician's evaluation of retrieved diagnostic data, the clinician may choose to modify certain parameters or otherwise modify the treatment of the patient.

As described below, the programmer 120 of a preferred embodiment allows the clinician to perform these various follow-up steps either manually (i.e., by interactively selecting each individual item to be displayed and test to be performed), or by using an "automated follow-up" feature which allows the clinician to semi-automatically follow a predefined follow-up protocol.

2. User Interface (FIG. 2)

Figure 2:
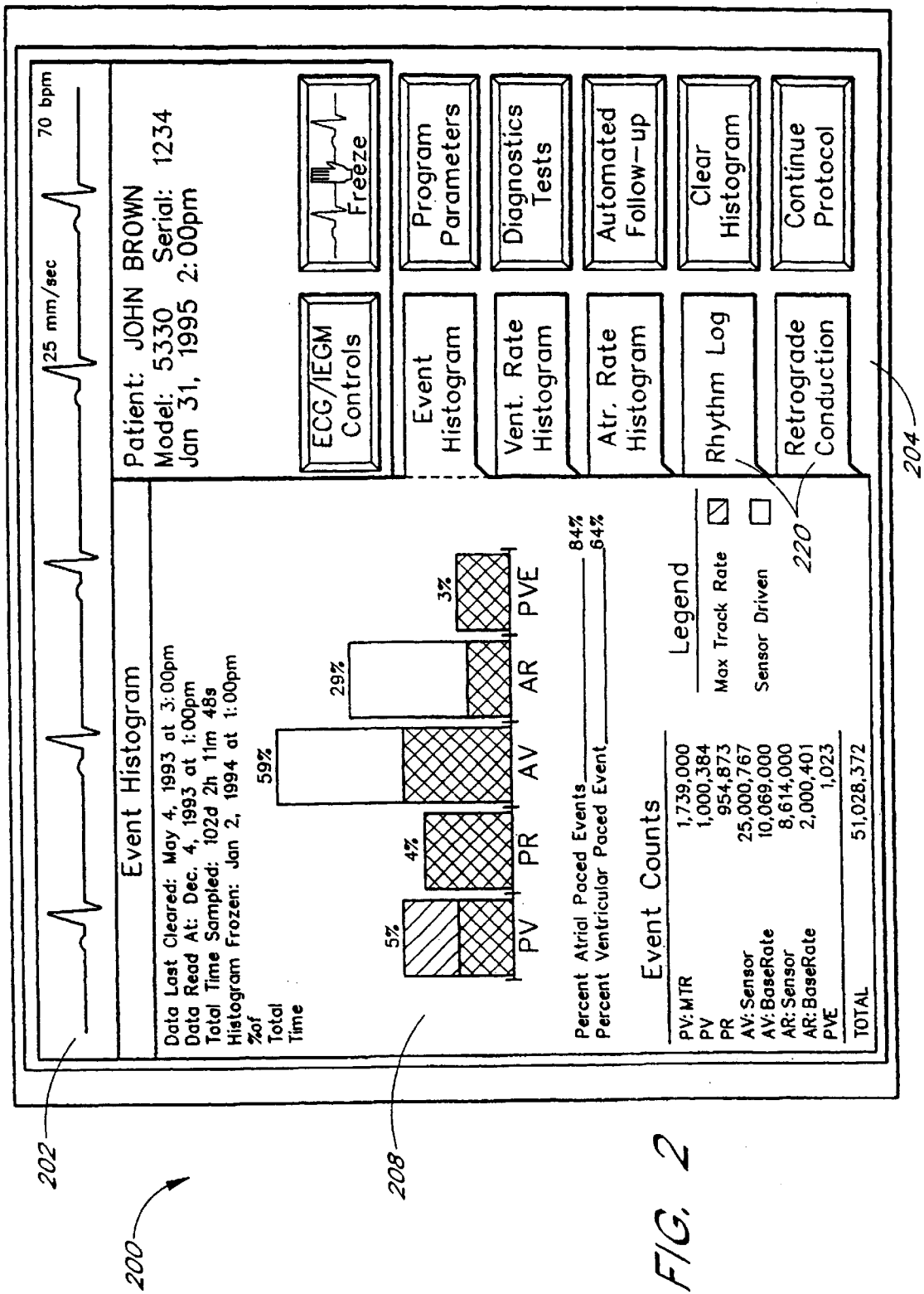
FIG. 2 is an example data display screen of the programmer's user interface.

In a preferred embodiment, the clinician interacts with the programmer 120 and the pacemaker 110 via a graphical user interface of the programmer 120, a representative display screen 200 of which is shown in FIG. 2. The clinician may also use a keyboard (not shown in FIG. 1) to enter remarks and other data. With reference to the EVENT HISTOGRAM display screen 200 of FIG. 2, which is illustrative of the general format of the display screens used for displaying diagnostic and parametric data, the display screen 200 includes three primary sub-screens or "panels:" a real-time data display panel 202, a control panel 204, and a foreground panel 208. The real-time data display panel 202 displays the ECG and IEGM signals (including markers) transmitted, respectively, by the ECG electrodes 132 (FIG. 1) and the pacemaker 110. (In the FIG. 2 example, only an ECG signal is shown).

The control panel 204 includes various control buttons 220 for allowing the clinician to view other display screens and to initiate other follow-up related events. For example, the clinician can select the "PROGRAM PARAMETERS" button to view the program parameters (via corresponding display screens) stored by the implanted device, or can select a "CLEAR HISTOGRAM" button to clear the displayed histogram from the memory of the implanted device. The control buttons 220 can be selected by depressing corresponding portions of the touch-sensitive screen 128 (FIG. 1), or by clicking on the buttons using a mouse 136 (FIG. 1) or other pointing device. The functions performed by some of the buttons are specific to the particular display screen/data item being viewed. (The term "data item" is used herein to refer generally to the diagnostic records, parameters sets and other viewable data sets that can be retrieved from the implanted device and displayed by the programmer.)

The foreground display panel 208 is used to display the data associated with the foreground operation being performed by the clinician. This data may include, for example, a scrollable graph generated as part of an atrial capture test, a retrieved histogram, or a set of parameters. Diagnostic records are displayed within this panel 208 in a preformatted manner, along with associated explanatory text which is hard coded within the programmer's display routines. In the FIG. 2 example, the diagnostic record (i.e., the event histogram data) is displayed in both graphical and tabular form, along with hard coded explanatory text (e.g., the phrase "data last cleared:") of the display screen 200. In general, each diagnostic data record that can be retrieved from the pacemaker is displayed using its own respective display screen (such as the EVENT HISTOGRAM display screen shown in FIG. 2). However, some diagnostic records can be viewed in multiple different formats via different display screens of the programmer.

The clinician can access the various data display screens either manually (by selecting the corresponding control buttons 220) or semi-automatically (by using the automated follow-up features of the programmer, which can be accessed by selecting the AUTOMATED FOLLOW-UP button). Regardless of the method used, when a data display screen is selected (such as the EVENT HISTOGRAM display screen of FIG. 2), the programmer 120 initially checks to see if the corresponding (diagnostic or parametric) data item has already been read from the implanted device into programmer memory. If the data item has already been retrieved (e.g., by background interrogation), it is immediately displayed via the display screen. If the data item has not been retrieved, the programmer begins retrieving the data item (or finishes retrieving the data item if retrieval has already been initiated), and then displays the data item via the display screen.

In addition to the display screens used for the display of diagnostic and parametric data items, the user interface includes display screens and controls which correspond to other types of tasks, including protocol generation (FIG. 4), file management, and diagnostic tests.

3. Automated Follow-Up (FIGS. 2–4)

One of the automated follow-up features of the programmer 120 involves the use of a pre-specified examination protocol, which may be either a custom protocol (previously specified by the clinician or another user) or a standard (non-custom) protocol provided with the programmer 120. To access this feature, the clinician initially selects an AUTOMATED FOLLOW-UP button (shown in FIG. 2); the clinician is then presented with various controls and display screens which allow the clinician to, for example, define a new protocol, view a list of existing protocols of a particular clinician (FIG. 3), display and edit the steps of a protocol (FIG. 4), and start a selected protocol.

Figure 3:
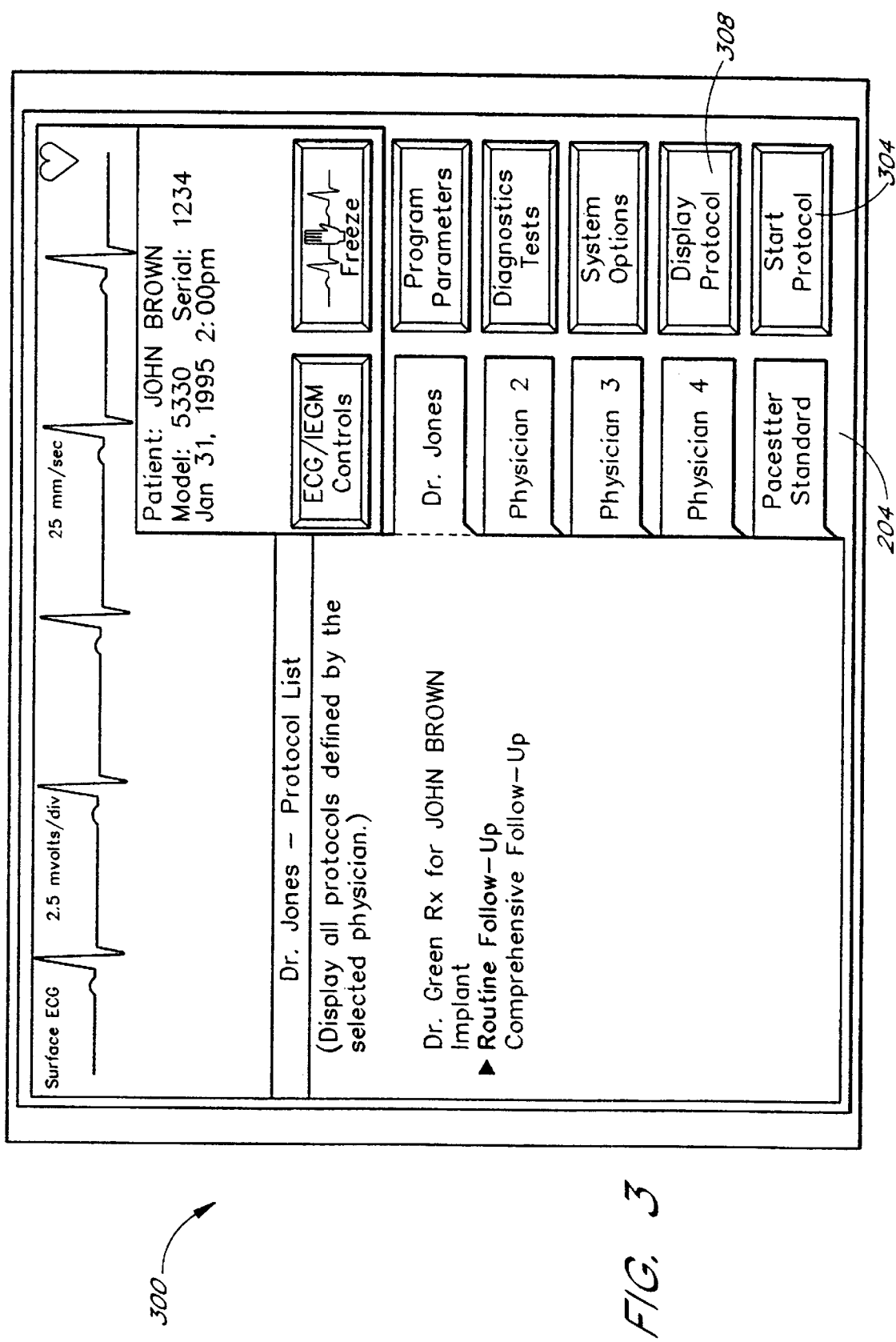
FIG. 3 is a programmer display screen which may be used to select between existing follow-up protocols.

FIG. 3 illustrates a protocol display screen which displays the predefined protocols of a particular clinician. In this example, the clinician (Dr. Jones) has four predefined protocols, each of which is stored as a respective protocol definition file on the Programmer's hard disk. In general, each protocol corresponds to a particular family of implantable device, which may be specified by the clinician prior to defining the protocol. Of course, any suitable naming convention and grouping method can be used for organizing the protocol definition files for display via the user interface. Using either the touch screen 128 or the mouse 136, the clinician can select any one of the displayed protocols. (In the FIG. 3 example, the "Routine Follow-up" protocol is selected.) The clinician can then use the "START PROTOCOL" button 304 to start the protocol (i.e., to begin the interrogation process), or use the "DISPLAY PROTOCOL" button 308 to display the steps of the protocol (as shown in FIG. 4).

Figure 4:
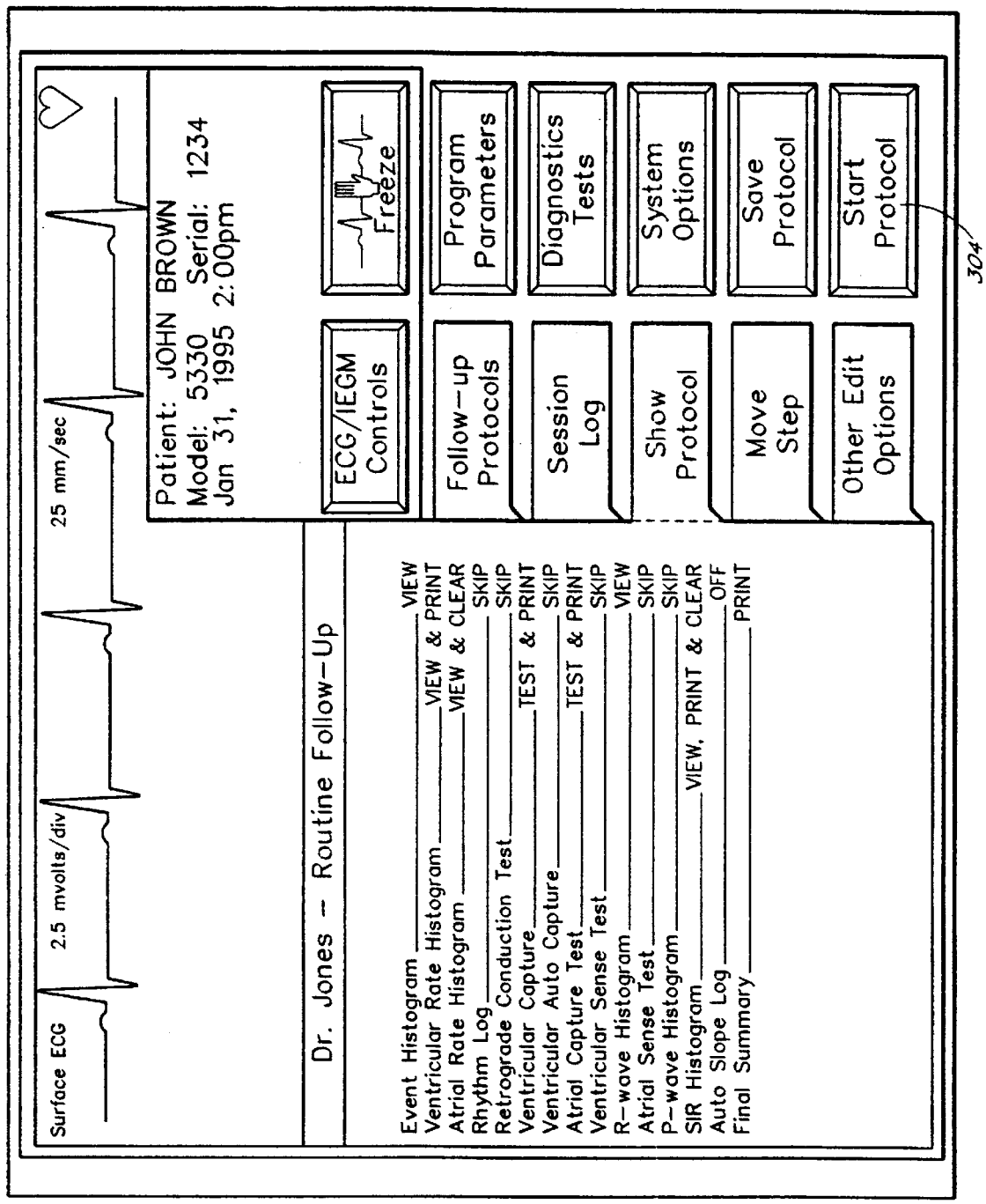
FIG. 4 is a protocol definition display screen of the programmer's user interface.

FIG. 4 illustrates a protocol definition screen, including an example follow-up protocol, in accordance with one embodiment of the system. From this display screen, the clinician can view the steps of the protocol, modify the protocol (using the MOVE STEP and OTHER EDIT OPTIONS BUTTONS, as described below), and/or start the protocol. The clinician can also generate new custom protocols by, for example, modifying the steps of the displayed protocol and then saving the modified protocol under a new filename.

As illustrated by the example protocol displayed in FIG. 4, each protocol generally comprises an ordered list of protocol steps, with each step including an identifier of a display screen (e.g., "EVENT HISTOGRAM" and "VENTRICULAR RATE HISTOGRAM") along with an action to be performed (e.g., VIEW or PRINT) with respect to the display screen. ("SKIP" indicates that no action will be performed. In other embodiments, only the protocol steps which include an action other than SKIP are displayed in the protocol definition screen.) In this example, the first automated action to be performed will be the retrieval and display of the event histogram, and the second automated action will be the retrieval, display and printing of the ventricular rate histogram.

In another implementation, the programmer 120 allows the clinician to separately specify an ordered list of the display screens to be printed. The clinician can thereby specify a print order which differs from the protocol's viewing order. This feature allows the clinician to flexibly specify the order of the printed display screens within a custom follow-up report. For example, the clinician can designate the "final summary" display screen (which summarizes the follow-up session) as the first page of the printed report, even though the display screen was viewed at the end of the follow-up session.

Table 1, which is attached at the end of this disclosure, lists a master set of the protocol steps (each corresponding to a respective display screen) that can be included in a custom protocol for the AFFINITY® family of pacemakers. (Earlier pacemakers from Pacesetter, Inc. generally support various subsets of these protocol steps.) Listed to the right of each protocol step are the options that can be specified by the clinician for each protocol step. Using edit buttons such as the MOVE STEP and SAVE PROTOCOL buttons of FIG. 4 (and other edit buttons that can be accessed by selecting the OTHER EDIT OPTIONS button), the clinician can create, modify and save follow-up protocols which include various combinations of these protocol steps. (Options designated with a star symbol are the default options which are used if no option is specified by the clinician.) During the protocol generation process, only those steps that are supported by the pre-specified family of implanted device are displayed to the clinician. The protocol steps and options listed in Table 1 represent one preferred implementation of the automated follow-up software, and are not intended as a comprehensive list of the types of actions that can be performed using the custom protocol feature.

Once a follow-up protocol has been initiated (using the "START PROTOCOL" button 304), the programmer 120 begins to retrieve the diagnostic and parametric data items of the protocol (using background interrogation, as described below) from the implanted device. As the data items are retrieved, the clinician can semi-automatically sequence through the various display screens of the protocol (to view the corresponding diagnostic and parametric data items and to conduct the corresponding tests) by simply selecting the "CONTINUE PROTOCOL" button (FIG. 2), which causes the next display screen of the protocol to be displayed.

In addition, the clinician can depart from the protocol (to, for example, view a non-protocol diagnostic record, or temporarily jump ahead in the protocol) at any time, and then return to the protocol by selecting the "CONTINUE PROTOCOL" button. Advantageously, selection of the CONTINUE PROTOCOL button will not cause any display screen to be re-displayed. Thus, for example, if the clinician jumps ahead in the protocol to view the event histogram, the programmer will subsequently skip over the event histogram screen when the clinician continues the protocol. As the clinician views the protocol display screens, the designated print screens are automatically printed in the background, in the order specified within the protocol.

If, during a follow-up session, a protocol is used which includes steps that are not supported by the implanted device, the programmer 120 automatically skips over the unsupported steps.

As indicated above, whenever the clinician follows a predefined protocol, the programmer 120 uses a background interrogation process to automatically retrieve the diagnostic and parametric data items corresponding to the protocol.

This feature advantageously enables the clinician to view some protocol items (e.g., a heart rate histogram, or a list of sensor parameters) while other protocol items are being retrieved by the programmer 120 in the background (transparently to the clinician). This in-turn reduces or eliminates the need for the clinician to wait for each data item to be retrieved—a process which typically takes a few seconds or more per retrievable data item. To maximize the benefit of this feature, the background interrogation is carried out in an order which corresponds to the viewing order specified within the protocol. Thus, for example, if the first display screen of the protocol is the event histogram screen, the programmer 120 retrieves the event histogram data first, and then automatically proceeds to retrieve the next protocol item.

Whenever, during the background interrogation process, the clinician initiates an operation (referred to as a "foreground operation") which requires the use of the telemetry channel, the background interrogation process is temporarily halted to allow the programmer (and clinician) to immediately perform the foreground operation. (The term "telemetry channel" refers generally to the hardware and software/firmware components used to transfer information between the programmer 120 and the implanted device by RF.) This situation arises, for example, when the clinician departs from (e.g., jumps ahead in) the protocol to view an item that has not yet been retrieved, or initiates a diagnostic test (which may or may not be part of the protocol) that makes use of the telemetry channel. This feature ensures that the step currently being performed by the clinician (i.e., the foreground step) is given the highest data transfer priority, so that the clinician need not wait unnecessarily for the retrieval of data items unrelated to the follow-up step being performed. As described below, this feature of the invention is implemented in-part using two device handler software tasks—one in charge of background interrogation and the other in charge of foreground telemetry operations—which contend with one another for control of the telemetry channel. Once the foreground telemetry operation has been completed, the programmer 120 automatically resumes the background interrogation process to retrieve the data items corresponding to the remaining protocol steps.

The programmer software can advantageously be configured by the user such that, once all protocol data items have been retrieved, the programmer 120 automatically retrieves all other diagnostic and parametric data items (in the background) stored by the implanted device; this advantageously allows the clinician to view non-protocol data items (e.g., at the end of the automated session) without having to wait for interrogation and data retrieval. When this option is selected, all of the retrievable data items stored by the implanted device reside within the programmer's memory at the end of the background interrogation process. (For an AFFINITY® pacemaker, the process of retrieving all of the pacemaker data by background interrogation typically takes about 45 seconds, assuming the background interrogation sequence is not interrupted.) The programmer automatically stores this data in a session log file (on the programmer's hard disk) for subsequent recall and use; thus, even if the clinician does not view all of the available diagnostic data during the follow-up session, the data can be viewed at a later time (e.g., during a subsequent patient visit).

While it is contemplated that the background interrogation feature will be most beneficial when used in conjunction with an automated follow-up protocol, it should be noted that the feature can also be used when no protocol is selected. For example, in one embodiment of the programmer 120, background interrogation is used to retrieve all of the pacemaker data (in a default order) whenever the clinician performs an initial interrogation of the implanted device.

Advantageously, the custom protocol and background interrogation features of the programmer 120 do not require any modification to the hardware or firmware of existing pacemakers. Thus, these automated follow-up features can be used in the examination of patients with a wide range of preexisting pacemakers, including, for example, pacemakers in the SYNCHRONY®, TRILOGY®, MICRONY®, SOLUS®, PARAGON®, PROGRAMALITH®, REGENCY®, PHOENIX®, SENSOLOG®, DIALOG® and MULTILOG™ families of Pacesetter, Inc. These features can also be used to facilitate data retrieval and analysis with other types of implantable devices, such as defibrillators, drug pumps, and neural stimulators.

4. Benefits of Automated Follow-Up Features

As will be readily appreciated by those skilled in the art, the above-described automated follow-up features provide a number of significant advantages over existing programmers and methods of use thereof. One advantage is a significant reduction in the interaction required between the clinician 102 and the programmer 120 to follow a particular protocol. This allows the clinician to focus on interviewing the patient 100, rather than being concerned with the menu selections needed to initiate the various diagnostic tests and to retrieve, view and print the various diagnostic data records.

Another advantage is a significant reduction in the time required to conduct a follow-up session. This reduction in time is the result of both (1) the reduction in the number of menu selections required on the part of the clinician, and (2) the data retrieval efficiency which results from the background-interrogation-related features of the programmer. In initial tests, it has been found that a follow-up protocol which normally takes 20 minutes when performed manually can be performed in roughly three minutes when the automated follow-up option is used.

In addition to the foregoing efficiency-related advantages, the automated follow-up features help to ensure that all of the clinically significant information stored by the pacemaker will be considered during the follow-up session. For example, for a physician that normally follows a follow-up protocol (manually), the feature will help to ensure that no step of the protocol is accidentally skipped, even if the physician temporarily departs from the protocol. Furthermore, as a result of the time savings and added convenience provided by the automated follow-up feature, it is believed that many physicians will take the time to view more of the diagnostic data records stored by pacemakers.

Additional details of the protocol and background interrogation features of the programmer 120 are set forth in U.S. Pat. No. 5,833,623, titled "System And Method For Facilitating Rapid Retrieval And Evaluation Of Diagnostic Data Stored By An Implantable Medical Device," which is incorporated hereby by reference.

5. Hardware Architecture (FIG. 5)

The hardware architecture of the programmer 120 will now be described with reference to FIG. 5.

Figure 5:
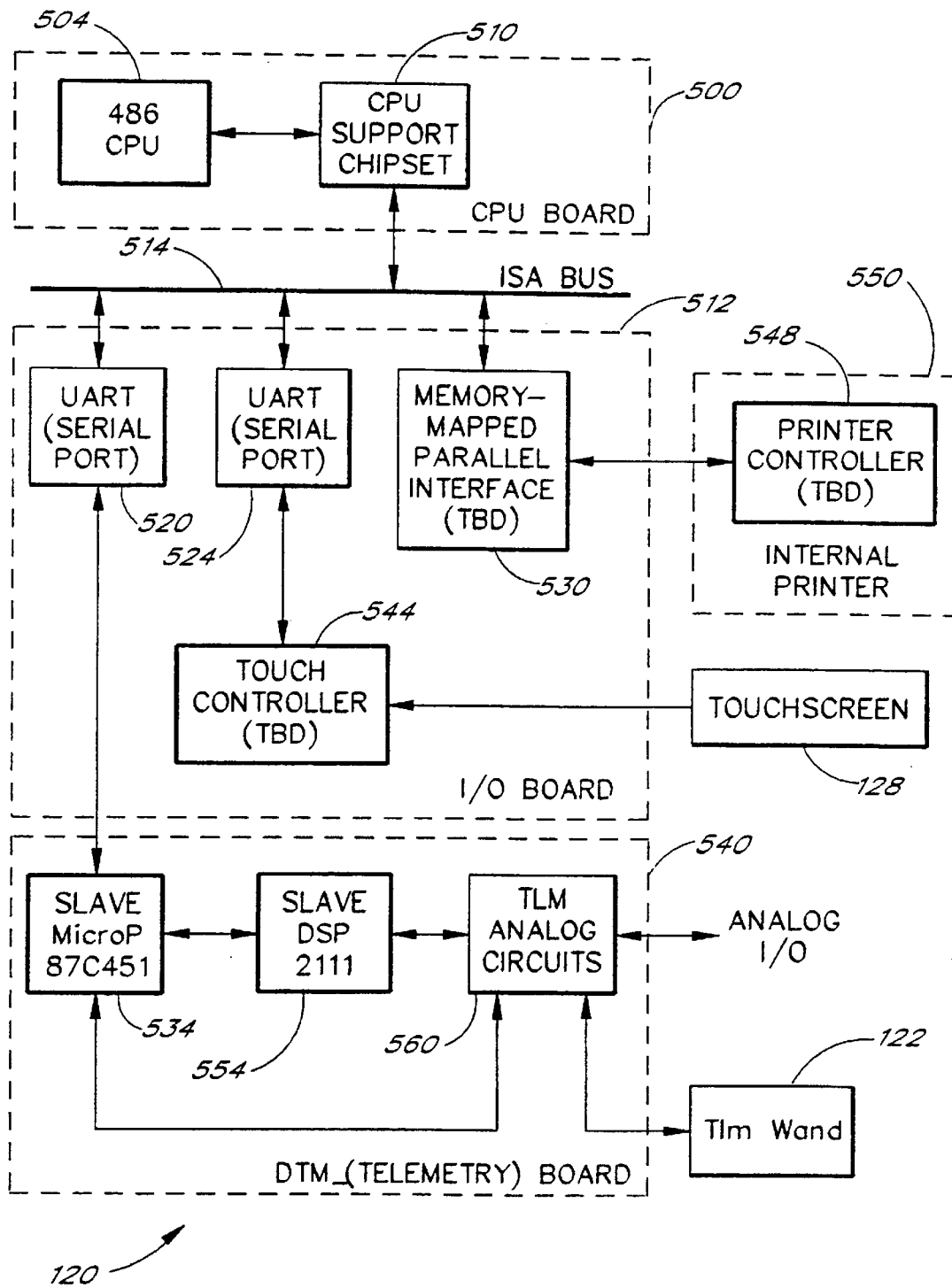
FIG. 5 is an architectural diagram of the primary hardware components of the programmer.

FIG. 5 is an overall system block diagram showing the main internal components of the pacemaker programmer 120. As shown in FIG. 5, the programmer 120 includes a central processing unit (CPU) board 500 which includes a 486 CPU 504, or the like. The CPU 504 communicates with a CPU chip set 510 which may, for example, include buffers, interface circuitry, random access memory (RAM), etc. In one embodiment, at least 16 megabytes of RAM are included in the CPU chip set 510 for use by the CPU 504.

The CPU board 500 communicates with an input/output (I/O) board 512 via an industry standard architecture (ISA) bus 514, with information being passed between the CPU 504 and the ISA bus 514 via the chip set 510. The ISA bus 514 communicates with UART (universal asynchronous receiver-transmitter) serial port interfaces 520 and 524, and a memory-mapped parallel interface 530. Each of the interfaces 520, 524, 530 acts as an interface between a peripheral unit and the CPU board 500. The serial port interface 520 communicates with a slave microprocessor 534 (e.g., an INTEL 87C451 microprocessor) within a telemetry hardware board 540.

The serial port interface 524 communicates with a touch controller 544 on the I/O board 512, which receives inputs from the touch screen 128. In one embodiment, the touch screen 128 is integrally formed with the main chassis 124 of the programmer 120 (not shown in FIG. 1). The memory-mapped parallel interface 530 acts as an interface between the CPU board 500 and a printer controller 548 within an internal printer 550. As illustrated in FIG. 1, the internal printer 550 is preferably integrally formed with the chassis of the programmer 120, although an external printer could alternatively be used.

The telemetry hardware board 540 includes the slave microprocessor 534, as well as a slave digital signal processor (DSP) 554 (e.g., a 2111 DSP) and telemetry analog circuitry 560. The microprocessor 534 communicates bidirectionally with the slave DSP 554, as well as with the telemetry analog circuitry 560. In addition, the slave DSP 554 communicates bidirectionally with the analog circuitry 560. The telemetry analog circuitry 560 transmits and receives RF signals via the telemetry wand 122.

In one preferred embodiment, the programmer 120 is provided with a communication port or device 321 (FIG. 6) which communicates with a hospital network. Via this modem, the clinician can readily view and/or update patient status information (e.g., transcribed medical reports, images of chest X-rays and ultrasound scans, follow-up session files from previous follow-up visits, etc.) available on the network.

In operation, the CPU 504 serves as a main control processor within the programmer 120. All other processors (including the printer controller 547, the touch controller 544, the DSP 554 and the slave microprocessor 534) act as slaves to the CPU 504. Inputs are provided to the CPU 504 from the printer controller 548, the touch screen 128, the telemetry wand 122 (via the slave microprocessor 534), the mouse 136 and an external keyboard (not shown in FIG. 5). In addition, information from a system clock; a CD-ROM, a hard disk, a floppy disk, or similar data storage devices; surface ECG electrodes; and/or other input/output devices can be supplied to the CPU 504.

The CPU 504 processes the information received via these inputs, and outputs instructions and data to each of the peripheral controllers 548, 544, 534 via the chip set 510, the ISA bus 514, and the I/O board 512. For example, the touchscreen controller 544 may transmit signals to the CPU 504 indicating that the clinician has touched the part of the touchscreen 128 which corresponds to a CLEAR HISTOGRAM button (FIG. 2) of the user interface. The CPU processes this input and in-turn instructs the slave microcontroller 534 to initiate transmission of a command from the telemetry wand 122 to clear a particular histogram from pacemaker memory.

The slave microprocessor 534 acts as a control processor of the telemetry hardware board 540. In a preferred embodiment, the slave microprocessor 534 controls the DSP 554 by sending the DSP 554 commands and data. The slave microprocessor 534 also can reset the DSP 554 to regain control of the DSP 554 in the event that the DSP 554 fails to respond properly. The program which is executed within the DSP 554 is preferably downloaded to the DSP 554 from the slave microprocessor 534. In like manner, the slave microprocessor 534 is monitored by the CPU 504, and the CPU 504 can reset the slave microprocessor 534 in the event that the code executing within the slave microprocessor 534 fails to operate properly. The code executed by the slave microprocessor 534 is downloaded to the microprocessor 534 from the CPU 504.

More specifically, the slave microprocessor 534 receives serial commands and data from the CPU 504, telemetry data output from the DSP 554, and signals from the analog circuitry 560. The slave microprocessor 534 processes commands from the CPU 504 and responds to these commands in accordance with requests issued by the CPU 504. In addition, a continuous stream of IEGM and surface ECG data is transmitted to the CPU 504 and to the analog outputs from the slave microprocessor 534. The slave microprocessor 534 also monitors the DSP 554 for correct operation, and reloads the DSP program upon a reset condition.

The DSP 554 manages a telemetry protocol at the telemetry frame level, and performs a variety of standard signal processing functions such as filtering IEGM received from the pacemaker 110 and ECG data received from the surface electrodes 132. The touch controller 544 (also referred to hereinafter as the "touch panel processor") serves as a decoder for the touch screen 128. When a user presses a point on the touch screen 128, this information is decoded by the touch panel processor 544 and sent to the CPU 504 via the serial interface 524. The printer controller 548 controls the operation of the internal printer hardware in response to instructions from the CPU 504. The telemetry wand 122 transmits and receives information to and from the pacemaker 110 via a conventional or available wireless communications link.

6. Software Architecture and Data Flow (FIGS. 6–16)

Figure 6:
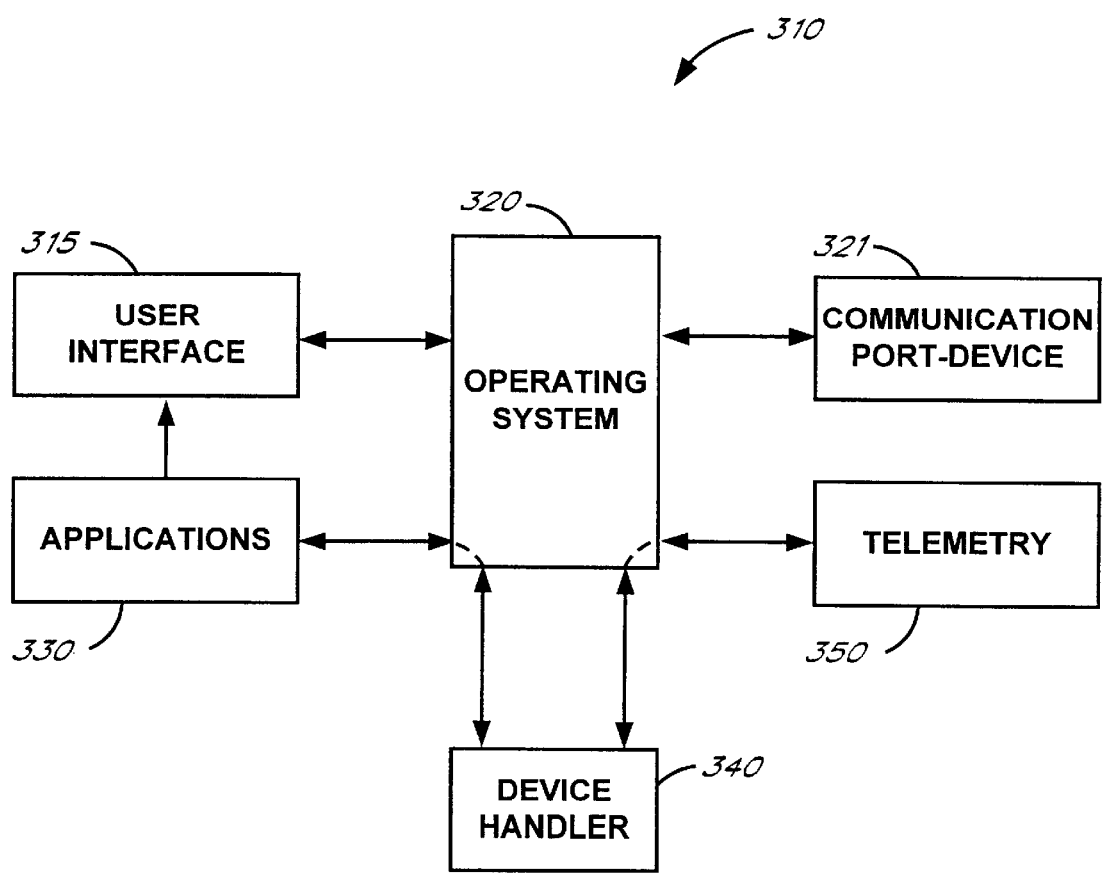
FIG. 6 is a high level schematic block diagram that illustrates an overview of the software architecture used in a preferred embodiment of the invention.

FIG. 6 is a high level schematic block diagram which illustrates an overview of a software system 310 (also referred to as processor) used in a preferred embodiment of the invention. The software system 310 includes a graphical user interface 315 which runs under the control of an operating system 320. In one embodiment, the operating system 320 may be implemented as the VxWorks® real time operating system available from Wind River Systems, Inc., located in Alameda, Calif. Applications subsystem 330 passes parameters and other information to the user interface 315 and also runs under the control of the operating system 320. A device handler module 340 accesses processes included within the applications module 330 using operation system objects to transfer control of the processes to the device handler module 340. A telemetry module 350 accesses processes within the device handler module 340 using operating system objects to transfer control of the processes to the telemetry module 350.

In operation, the user interface module 315 includes routines and tasks which are used to control the display of data on the touch-screen monitor 128, as well as the input of data received via the touch-screen monitor 128, the mouse 136, an external keyboard, permanent buttons on the programmer 120, etc. For example, if the user touches a certain place on the touch screen 128, the user interface determines which operation is to be performed based upon the coordinates of the location touched by the user.

The user interface 315 calls application processes and subroutines within the applications module 330 to perform some of the input/output and display operations required by the user interface module 315. The operating system 320 is used to command the execution of routines and tasks, and also provides resource allocations amongst the various modules. Communication between tasks, with the exception of the output from the applications module 330 to the user interface 315, is through interprocess communication facilities provided by the operating system 320. In one preferred embodiment, the user interface module 315, the operation system 320, and the processes within the applications module 330, are all executed within the central processing unit 504 (FIG. 5).

The device handler module 340 includes processes and subroutines which are executed within the CPU 504 to manage control of the peripheral devices such as the printer 550, the touch screen 128, and the telemetry wand 122. A device handler module 340 may access applications, processes and subroutines stored within the applications library module 330 in order to manage each of the peripheral devices connected to the pacemaker programmer 120.

The telemetry module 350 includes processes and subroutines which are used to directly control the operation of the telemetry hardware board 240, as well as the telemetry wand 122. The processes and subroutines within the telemetry module 350 execute within the slave microcontroller 235 or the slave DSP 255. Different tasks, processes or subroutines within the device handler module 340 can be accessed from the telemetry module 350 via the operation system 320.

The various automated analysis and programming features of the invention will now be described with reference to the flowcharts of FIGS. 7–20.

Figure 7:
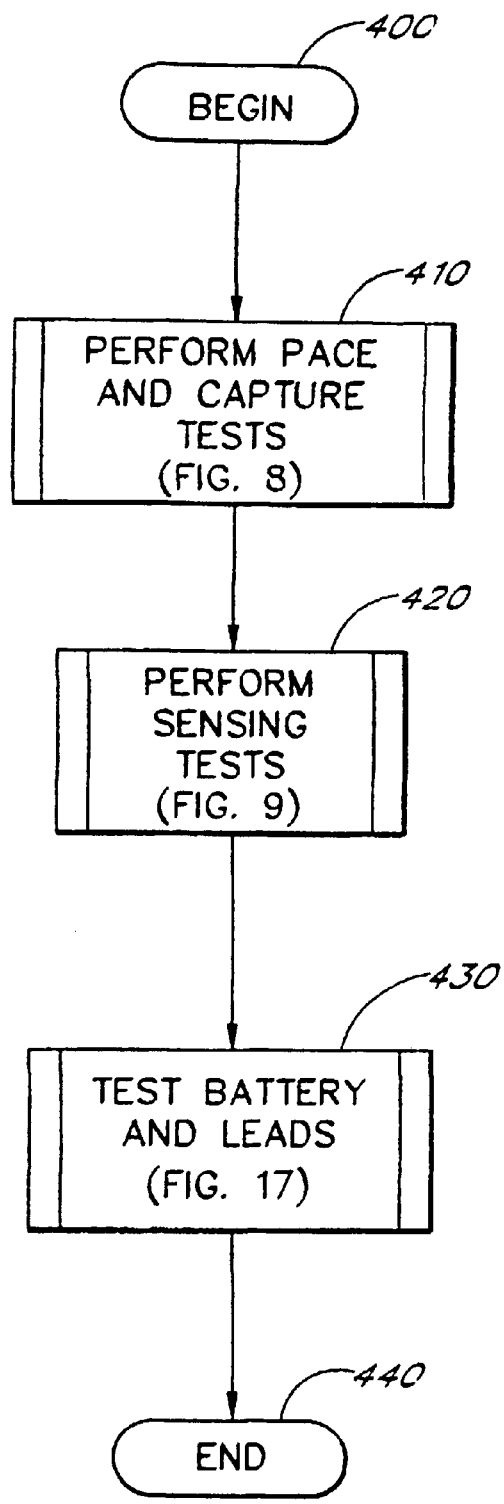
FIG. 7 is a flowchart which illustrates the overall method employed by a preferred embodiment of the present invention for a cardiac stimulation device, such as a pacemaker, which is providing dual-chamber pacing with atrial tracking and which is pacing and sensing in both the atrium and the ventricle with an inhibited or triggered response to sensing.

FIG. 7 is a flowchart which illustrates an example sequence of tests that may be performed during a follow-up visit, and will be used to describe the automated analysis and programming features of the programmer 120. Typically, these tests will be part of a custom or standard protocol, and will be interleaved with protocol steps that involve the retrieval of histogram and other diagnostic data. For purposes of this illustration, however, it may be assumed that the tests listed in FIG. 7 are the only steps of the predefined protocol.

It may also be assumed that the follow-up examination is in connection with a pacemaker which is providing dual-chamber pacing with atrial tracking, and which is pacing and sensing in both the atrium and the ventricle with an inhibited or triggered response to sensing. In this pacing mode, in the absence of intrinsic activity, both chambers are paced at the program base rate. Intrinsic atrial activity (i.e., electrical stimuli provided to the cardiac tissue by the natural operation of the heart) during the atrial alert period inhibits the pacemaker atrial output.

Furthermore, the interval used to measure the time between the last ventricular sensed or paced event and the delivery of the next atrial pulse (commonly referred to as the atrial escape interval) is terminated to initiate the AV delay (i.e., the interval used to measure the time between the last atrial sensed or paced event and the delivery of the next ventricular pulse). This pacing mode is typically referred to as DDD pacing.

As depicted in FIG. 7, in response to initiation of the protocol by the physician, the programmer 120 performs pace and capture tests, as represented within a subroutine block 410. A pace and capture test is a test which is used to determine when a pulse generated by the pacemaker 110 is at a sufficient amplitude to produce a ventricular or atrial beat within the patient's heart 115. The method employed within the subroutine block 410 will be described in greater detail below with reference to FIG. 8.

Once the programmer 120 completes the pace and capture tests, the programmer 120 proceeds to perform sensing tests, as represented within a subroutine block 420. The sensing tests are used to verify the sensitivity of the pacemaker 110 in accurately sensing and recording electrical activity in the heart. Thus, the method performed within the subroutine block 420 verifies the ability of the pacemaker to recognize and respond to the electrical activity of the patient's heart 115. The manner in which the pacemaker 110 responds to the sensed signals depends upon the program mode and parameters of the pacemaker 110. The method employed within the subroutine block 420 will be described in greater detail below with reference to FIG. 9.

The programmer 120 tests the hardware within the pacemaker 110 to ensure that, for example, the battery is charged and the leads of the pacemaker 110 are operational. This method is represented within a subroutine block 430 and will be described in greater detail below with reference to FIG. 17. The method terminates, as represented within an end block 440.

Figure 8:
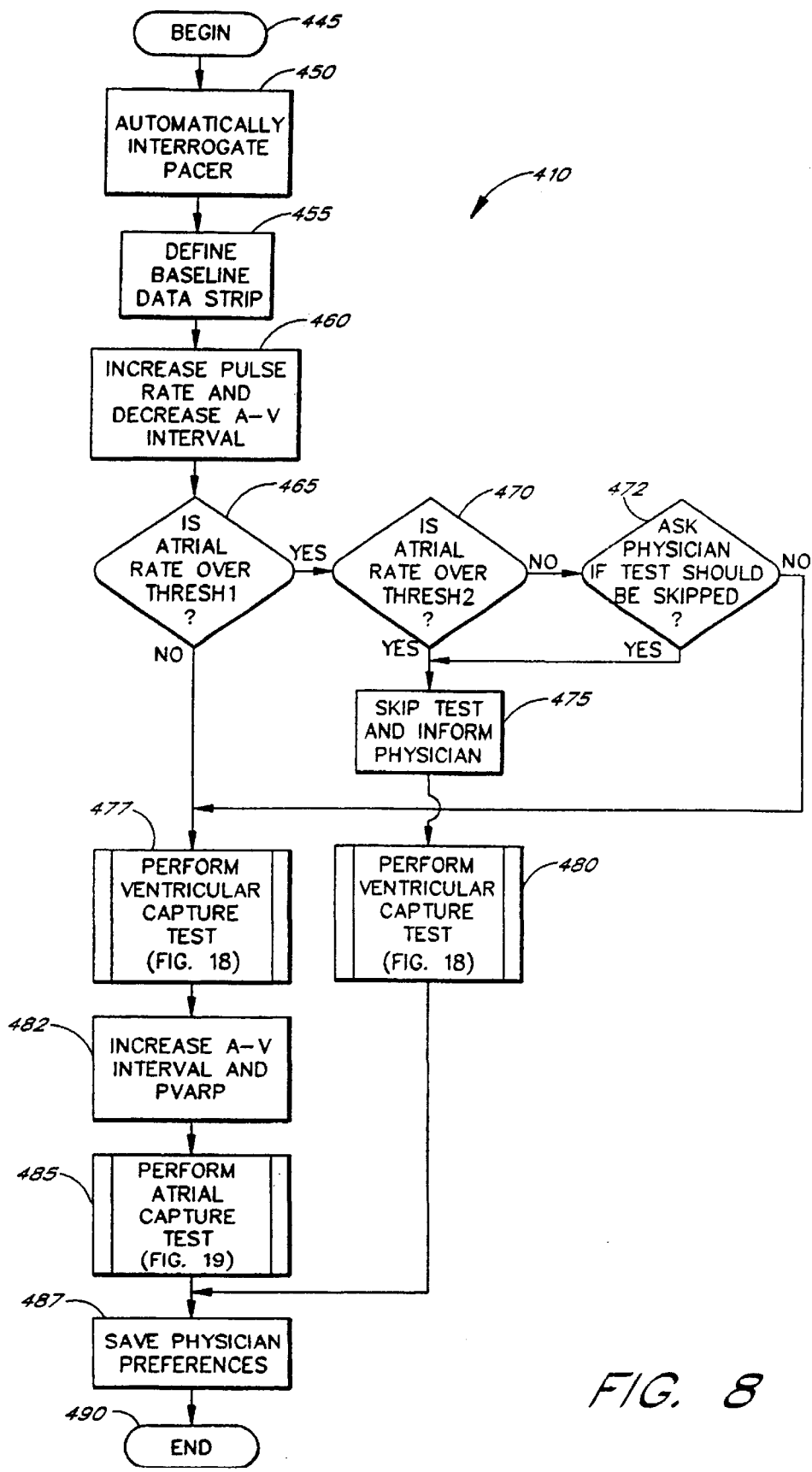
FIG. 8 is a flowchart which illustrates in greater detail the method used to perform the pace and capture tests represented in the subroutine of FIG. 7.

FIG. 8 is a flowchart which illustrates in greater detail the method used to perform the pace and capture tests represented in the subroutine block 410 of FIG. 7. As used herein, capture is the induction of an electrical depolarization of the cardiac chamber which is being stimulated. Capture threshold, whether ventricular or atrial, refers to the lowest output of the pacemaker 110 which results in consistent capture. In order to assess the capture threshold, it is important to first confirm the presence of pacing. While this can be achieved by monitoring the surface ECG, there are occasions when an indirect marker of capture can be utilized. Depending on the lead which is being monitored during this evaluation, the pacemaker induced complex, which is also called an evoked response, may or may not be visible on the ECG. This is most common when assessing atrial capture as the evoked P wave tends to be significantly smaller than the paced QRS complex. It may be necessary to examine a number of surface ECG leads to determine which one provides the best visualization of the effective depolarization.

Another technique for confirming capture is to look at known electrophysiological events that should be associated with a specific phenomenon. For example, if there is atrial pacing, and AV nodal conduction is intact, each atrial output, assuming that capture is present, should be followed by a conducted QRS complex at an interval that approximates the normal PR interval even if a P wave is not visible in the EGG lead that had been selected. In the case of ventricular pacing, a visible T wave representing repolarization means that there had to have been an effective depolarization, even if the evoked QRS complex is isoelectric in the given lead that is being monitored.

If the entire pacemaker 110 or a specific channel of the pacemaker is being inhibited, it becomes important to reprogram the pacemaker 110 to demonstrate capture if an assessment of the capture threshold is desired. With respect to atrial pacing in either a dual or single chamber pacing system, it may be necessary to increase the rate. The rate is increased at least 20 BPM above the intrinsic rate to minimize the chance of a waxing and waning sinus arrhythmia that confuses the evaluation by periodic inhibition of the pacemaker 110. For ventricular capture in a dual chamber system with intact AV nodal conduction, shortening the paced or sensed AV delay until there is a clear change in the morphology of the ventricular complex confirms the presence of capture. Once this is achieved, the output is either manually or semi-automatically decreased until loss of capture is observed on the ECG, the test sequence terminated, and the output returned to an appropriate level.

In this setting, the capture threshold is commonly taken as the last output setting at which there was stable capture. The capture threshold determined by a progressive decrease in the output (down-threshold) may be lower than the capture threshold measured when starting from a loss of capture and progressively increasing the output (up-threshold) due to a phenomenon called the Wedensky effect. Although these two values are commonly very close, a rare patient can show a marked difference between the two values with the up-threshold being higher than the down-threshold.

The capture threshold is not a fixed number. Rather, it may wax and wane during the course of the day. The measurement reflects the minimal amount of energy that is required to be delivered to the heart to assure effective capture at a particular moment in time. Energy is a function of current, voltage and pulse duration (time). The two parameters that can be independently controlled and programmed by the physician are pulse amplitude or voltage and pulse duration. As such, capture is reported in terms of either voltage or pulse duration.

The relationship between these two parameters can be defined by a "strength-duration" curve. At a very narrow pulse duration, a very high pulse amplitude will be required. As the pulse duration is progressively increased, the required voltage decreases but not in a linear manner. The relative rate of decrease progressively slows until a pulse duration is achieved where the pulse voltage needed for capture will not decrease further. If the pulse duration continues to be increased, the pulse voltage will remain at this fixed level. This is called the rheobase, and the pulse duration threshold at twice the rheobase is called the chronaxie point. The chronaxie point generally ranges between approximately 0.3 ms and 0.5 ms. As the thresholds fluctuate, both on a daily basis with changing sympathetic and parasympathetic tone as well in response to disease processes, they tend to follow parallel curves. The programmer 120 can provide graphs of the strength-duration curve with a 2:1 and 3:1 safety margin curve being simultaneously displayed. The capture safety margin is a ratio defined by the programmed output divided by the measured threshold level. The capture safety margin is expressed in units that are either the programmed voltage or pulse width; however, other units such as energy can also be used.

In a pacemaker dependent patient, the usual recommendation for a conventional pacemaker that cannot automatically monitor the status of capture and adjust its output, is to set the pacemaker to provide a 2:1 safety margin with respect to the voltage threshold. This is a voltage that is 100% above the measured threshold voltage, although certain studies, such as Danilovic D, Ohm OH, Pacing threshold trends and variability in modern tined leads assessed using high resolution automatic measurements, conversion of pulse width into voltage thresholds, PACE 1999; 22: 567–587, have recommended a 150% to 200% safety margin to protect the patient from unexpected late threshold rises that may occur even with the present generation of steroid-eluting leads.

The concept of safety margin is not a guarantee that the capture threshold will not rise above the programmed output of the pacemaker. If the goal is to maximize patient safety, the output of the pacemaker should be programmed to its highest allowed level. This, however, will increase the power drain and accelerate the rate of power source depletion. If the capture threshold is stable at a very low level, a high output is wasteful and will unnecessarily shorten the pulse generator longevity.

The concept of safety margin attempts to weigh the anticipated waxing and waning of capture thresholds once the capture threshold is stable in an effort to protect the patient while maximizing the longevity of the implanted pulse generator by reducing the output and therefore reducing the power source drain. Hence, in the pacemaker dependent patient, a 2:1 or higher safety margin has been recommended. For the patient who has never been demonstrated to be dependent on the pacemaker, it may be safe to set the pacemaker to a lower output and a narrower safety margin. The degree to which the output is reduced is a direct function of the effective reduction in the power drain associated with the lower outputs. If the reduction is minimal and will not significantly enhance the projected longevity of the pacemaker, there is little to be gained by a marked reduction in the output. On the other hand, if the projected increase in longevity is longer than a predetermined period of time such as 1 year, it might be reasonable to decrease the output consistent with patient safety.

The automatic capture feature of the present invention reduces the need for periodic capture threshold assessments, and further reduces the need to consider the combined concerns of patient safety and device longevity. According to one embodiment, the pacemaker 110 automatically adjusts its output to approximately 0.25 Volts above the measured capture threshold, which is a working margin and not a safety margin. The ventricular capture threshold is automatically measured every eight hours unless there is a detected threshold rise, and then it is determined as often as needed, allowing the pacemaker 110 to maintain capture while keeping the output as low as possible.

A preferred way to maintain a narrow working margin safe is for the pacemaker 110 to monitor the presence or absence of capture on a beat-by-beat basis. Should the pacemaker 110 detect noncapture, it delivers a relatively high output back-up pulse shortly after the diagnosis of noncapture on a primary pulse. The back-up pulse is approximately 4.5 Volts which often provides a greater safety margin than the clinical standard of 2:1. As the usual output of the pacemaker 110 is very low, the overall impact on the battery current drain associated with the microprocessor controlled algorithm is minimal with a significant net increase in pulse generator longevity over that which would be achieved with a 2:1 safety margin. The behavior of the pacemaker 110 can be visualized during an automatic capture threshold evaluation initiated via the programmer 120 at the time of a follow-up evaluation, as is described herein in connection with FIGS. 8, 18, and 19.

With reference to FIG. 8, the submethod initiates, as represented by a begin block 445, and thereafter the programmer 120 automatically interrogates the pacemaker 110 to retrieve the parameters, as represented within an activity block 450. The programmer 120 retrieves each of the parameters and data history stored in the memory within the pacemaker 110 via the telemetry link (or wand) 122.

Once the programmer 120 has interrogated the paced parameters, the programmer 120 defines a baseline data strip, as represented within an activity block 455. A baseline data strip includes the data taken for the ECG, IEGM, and corresponding markers while the patient is in the normal resting state, and is used as a reference against which unusual or abnormal states may be measured. This baseline may comprise paced and/or sensed data in the atrial channel, as well as paced and/or sensed data in the ventricular channel. Both the heart rate and the PR interval (i.e., the period of time measured from the onset of atrial depolarization to the onset of ventricular depolarization) are measured by the programmer 120. In accordance with a preferred embodiment of the invention, both sensed and paced beats can be analyzed when the sensitivity is monitored. Likewise, paced beats can be analyzed for capture verification.

Once the baseline data strip has been defined within the activity block 455, the programmer 120 instructs the pacemaker 110 to increase the pulse rate and to decrease the AV interval as represented within an activity block 460. The AV interval is the length of time between an atrial paced event and the delivery of a ventricular output pulse. For sensing purposes, the AV interval is defined as the length of time measured between an atrial sensed event and the delivery of a ventricular output pulse. Since the method described in FIG. 8 is a method of performing pace and capture tests, however, the decrease of the AV interval means that the programmer 120 decreases the length of time between the atrial paced event and the delivery of a ventricular output pulse. The AV interval is also referred to herein as the AV delay. The purpose of increasing the pulse rate and decreasing the AV interval is to overdrive both chambers of the patient's heart 115 to obtain a data strip. This step allows capture to be verified in both chambers, even if the output pulses are masked by sinus rhythm and/or AV conduction. Furthermore, by increasing the pulse rate and decreasing the AV interval, the likelihood of fusion beats in both chambers of the patient's heart 115 is substantially reduced. When the data strip is obtained, only the surface ECG and markers are analyzed during this step, since it is likely that the IEGM output signals are saturated after the pacing spikes. The surface ECG is analyzed to verify that every pacer pulse on the marker data is followed by an evoked response at the appropriate time. A failure to capture in the ventricle in the presence of intact AV conduction, for example, will show up as a lengthening of the time between the ventricular stimulus to the evoked response. If the AV delay had not been shortened, this determination would be more difficult. Thus, the decrease in the AV interval and the increase in the pulse rate increases the ability of the programmer 120 to verify that every pacer pulse is followed by an evoked response at the appropriate time.

Once the pulse rate has been increased and the AV interval has been decreased, a determination is made if the atrial rate is above a prespecified threshold value, as represented within a decision block 465. If the measured atrial rate is high enough that the overdrive rate would be above this predetermined limit, then the physician 102 is asked if he wishes to skip the determination of atrial capture. Thus, if the atrial rate is over the predefined threshold value, a further determination is made if the atrial rate is above a second, higher predefined threshold value, as represented within a decision block 470. However, if the atrial rate is not above the first threshold value, the method proceeds according to the normal fashion, and the ventricular capture test is performed, as represented within a subroutine block 477.

If it is determined within the decision block 470 that the atrial rate is above the second threshold value, then the atrial capture test would be automatically skipped, as represented within an activity block 475. In the event that the atrial capture test is automatically skipped, the physician 102 is informed by a message on the display screen 128. However, if the atrial rate is not over the second predefined threshold value, then the physician 102 is asked if the atrial capture test should be skipped, as represented within a decision block 472. If the physician decides that the atrial capture test should be skipped, then the method proceeds to the activity block 475, which causes the atrial capture test to be skipped and which confirms that the test has been skipped with a message to the physician on the display screen 125. However, if the physician 102 determines that the atrial capture test should not be skipped, then the method proceeds to the subroutine block 477, wherein the ventricular capture test is performed.

If the physician 102 has determined that the atrial capture test should be skipped, the ventricular capture test is still conducted, as represented within a subroutine block 480 which is entered from the activity block 475. However, if the ventricular capture test is performed as represented within the subroutine block 480, the atrial capture test will not be performed after the ventricular capture test, as is the case with the ventricular capture test performed within the subroutine block 477. Other than this difference, the method employed within the subroutine block 477 is substantially the same as the method employed within the subroutine block 480 and will be described in greater detail below with reference to FIG. 18. Because the AV delay has been decreased, loss of capture will result in an increase in the measured time between the ventricular stimulus to the evoked response. This measurement is performed in order to provide an automatic measurement of ventricular capture safety margin. According to one preferred embodiment of the invention, if the analysis program does not observe an evoked response within a predefined period (e.g., 100 milliseconds), then a command is sent by the programmer 120 to the pacer 110, which causes the pacer 110 to provide a back-up pulse to the ventricle at a higher voltage. This avoids an excessive prolongation of the ventricular contraction in the absence of intact conduction. In an alternative embodiment of the invention, if the programmer 120 does not observe an evoked response within the same predetermined time period, then the ventricular amplitude is restored, and the rate of the output pulses produced by the pacemaker 110 is increased to minimize the pause in the ventricular contraction rate.

Once the ventricular capture test has been performed, as represented within a subroutine block 477, the AV delay is increased, as is the post-ventricular atrial refractory period (PVARP), as represented in an activity block 482. The PVARP constitutes one of the timing cycles in dual-chamber pacemakers during which the atrial channel's sensing circuitry is rendered unresponsive. Initiated by a sensed or ventricular paced event, and ending with an atrial sensed or paced event, the PVARP is intended to prevent the atrial-sensed amplifier from sensing far afield ventricular signals. Thus, the PVARP may be considered as the atrial equivalent of the ventricular blanking (i.e., the period in which the ventricular sense amplifier is temporarily disabled during the delivery of an output pulse so that signals from the opposite chamber are not detected). If the PVARP is sufficiently long, it can prevent the atrial channel from responding to premature atrial contractions or retrograde atrial depolarization, and thus prevent pacemaker-mediated tachycardias. Once the AV interval and the PVARP have been increased, the atrial capture test is performed, as represented within a subroutine block 485. The method employed within the subroutine block 485 to perform the atrial capture test will be described in greater detail below with reference to FIG. 19. Because the pulse rate has been increased and the AV delay has been increased, a loss of atrial capture will result in a delay in the atrial evoked response and a delay in the conducted R-wave (assuming intact AV conduction is present).

It should be noted that the PVARP could be lengthened for the entire testing procedure, since the patient 100 is at rest. The lengthening of the PVARP would therefore prevent tracking of retrograde P-waves. This concept is an improvement which can also be applied to semi-automatic or automatic pace and sensing tests without the automatic analysis described herein.

In one embodiment of the invention, when loss of atrial capture is detected, a command is sent to the pacemaker 110, which causes the pacemaker 110 to produce an atrial stimulation pulse at an increased amplitude after a predetermined time (e.g., 100 milliseconds). If the programmer 120 is relying on R-wave measurements to determine atrial capture, then the atrial stimulation pulse would be provided with the ventricular stimulus pulse. In an alternative embodiment, when the loss of atrial capture is detected, the atrial amplitude is restored and a PVC (premature ventricular contraction) response is initiated in the pacemaker 110 by external control signals from the programmer 120 following the ventricular stimulus (i.e., the R-wave) in order to prevent retrograde conduction from starting a pacemaker-mediated tachycardia. In yet another embodiment of the invention, when loss of atrial capture is detected, the atrial amplitude is restored and the AV delay is substantially shortened to prevent retrograde conduction.

Since a trade-off exists between the number of cycles at each pulse amplitude during capture threshold determination and the test time, one aspect of the present invention involves saving physician preferences within the programmer 120 and also within the pacemaker 110 so that the physician 102 can initiate a patient-specific override. Other physician preferences, such as the first and second predefined thresholds, are similarly saved in the programmer 120 and/or the pacemaker 110. The saving of physician preferences is represented within an activity block 487, which may be entered from the atrial capture test subroutine 485 or directly from the ventricular capture test subroutine 480. Once the physician preferences have been saved, the method for performing ventricular and atrial capture tests terminates, as represented within an end block 490.

Figure 9:
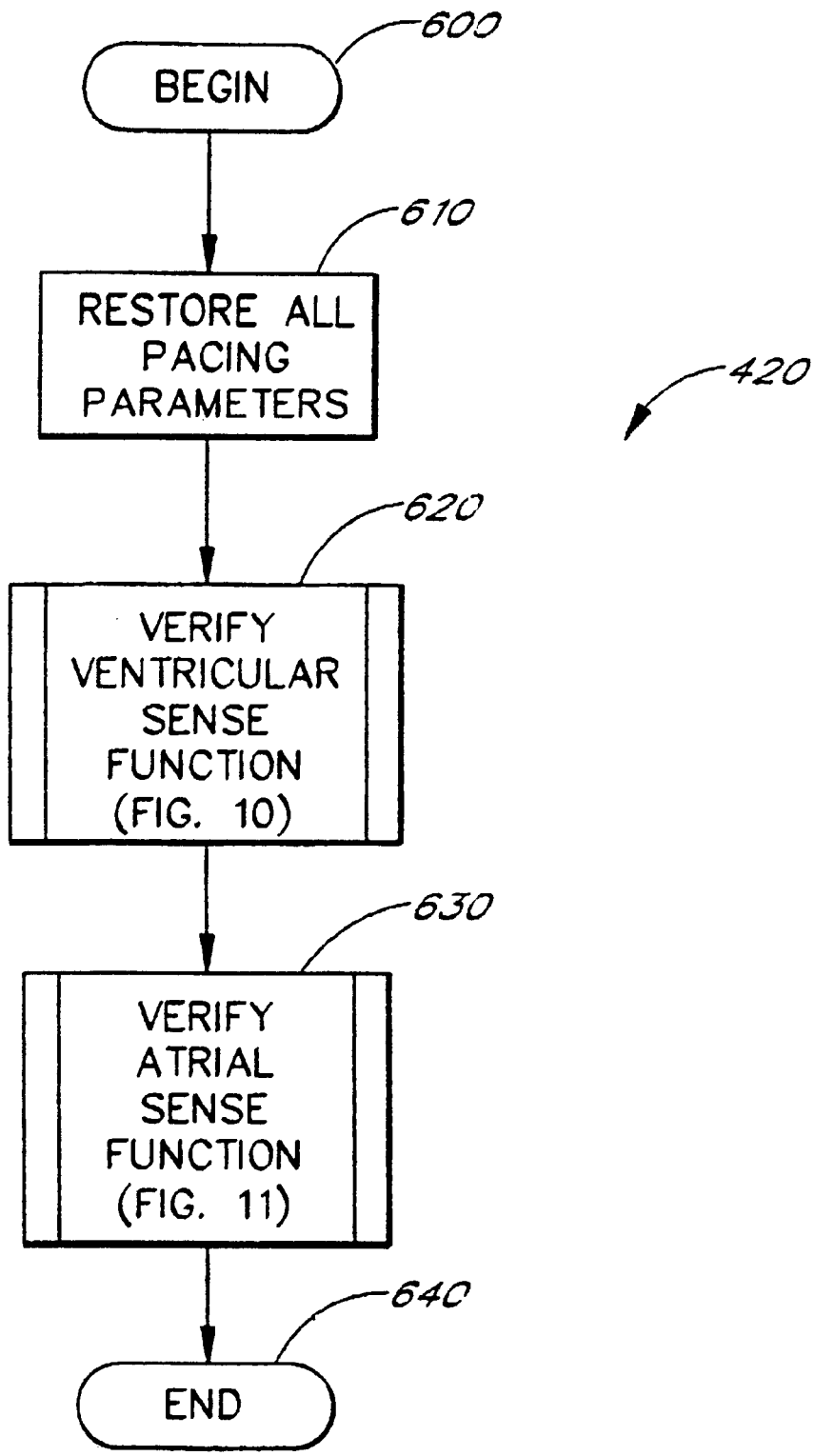
FIG. 9 is a flowchart which illustrates the overall method used in a preferred embodiment to perform sensing tests within the subroutine block of FIG. 7.

FIG. 9 is a flowchart which illustrates the overall method used in a preferred embodiment to perform sensing tests within the subroutine block 420 of FIG. 7. As depicted in FIG. 9, the method initiates as represented by a begin block 600, and thereafter all pacing parameters are restored to their original values, as represented within an activity block 610. The restoration of all pacing parameters to their initial values allows the programmer 120 to reestablish the baseline data strip which was initially established at the commencement of the pacing capture tests described above. Thus, after a predetermined number of cycles, the baseline strip is again analyzed. Thereafter, as represented within a subroutine block 620, ventricular sensing is verified. The method of verifying ventricular sensing will be described in greater detail below with reference to FIG. 10. Atrial sensing is verified, as represented within a subroutine block 630. The method employed to verify atrial sensing will be described in greater detail below with reference to FIG. 11. Once ventricular sensing and atrial sensing have been verified, the method terminates, as represented within an end block 640.

Figure 10:
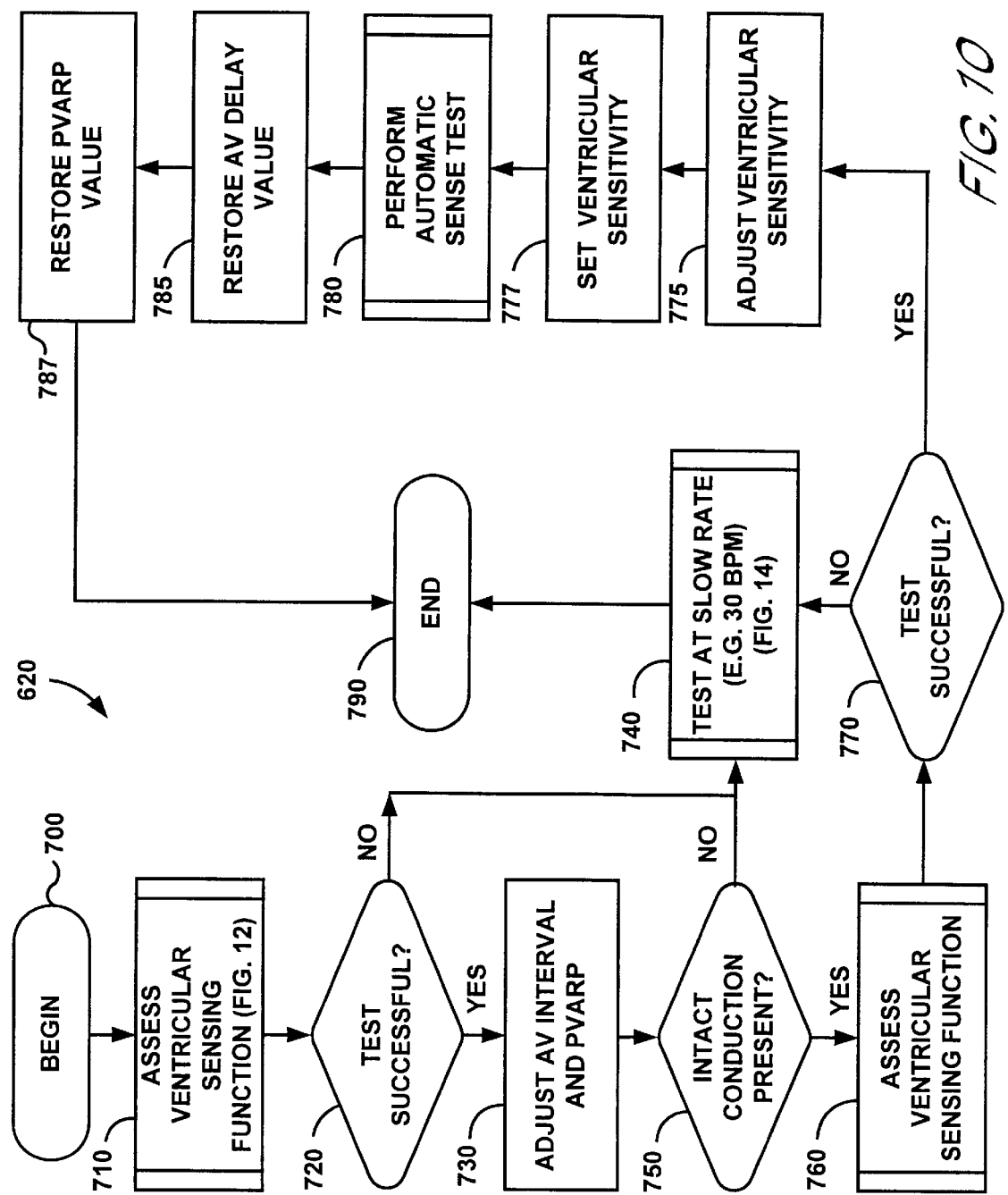
FIG. 10 is a flowchart which illustrates, in greater detail, the method employed within the subroutine block of FIG. 9 to determine the ventricular sensitivity threshold of the cardiac stimulation device.

FIG. 10 is a flowchart which illustrates, in greater detail, the method employed within the subroutine block 620 of FIG. 9 to determine the ventricular sensitivity threshold of the programmer 110. The ventricular sensitivity threshold method initiates as represented by a begin block 700, and ventricular sensing is assessed as represented within a subroutine block 710. The method by which ventricular sensing is assessed will be described in greater detail below with reference to FIG. 12.

Once ventricular sensing has been assessed, a determination is made, as represented within a decision block 720, if the test was successful. If ventricular sensing was confirmed so that the pacemaker 110 accurately senses each of the significant electrical events within the patient's heart 115, then the method proceeds to automatically determine an optimum AV delay value by increasing the AV interval either gradually in steps, or directly, to a predetermined or programmable value. In one embodiment, the optimum AV delay value ranges between 300 and 350 msec. Thereafter, the method automatically adjusts the AV delay to the optimum AV delay value, and further increases the AV interval and PVARP, as represented by an activity block 730. In one embodiment, the optimum AV delay is the value at which R sensing occurs, and is determined by having the pacemaker 110 gradually increase the AV delay until the R wave is detected. If the test was determined to be unsuccessful, the testing is performed again at a slower rate, as represented by a subroutine block 740. The method employed within the subroutine block 740 to test ventricular sensing at a slower rate will be described in greater detail below with reference to FIG. 14.

If it is determined within the decision block 720 that the test is successful, and the AV interval and PVARP have been increased, then a further test is performed, as represented by a decision block 750, to determine if intact conduction is present. Intact conduction occurs when electrical stimulus initiated in the atrium is transmitted to the ventricle. If intact conduction is not present, then the method enters the subroutine block 740 to test ventricular sensing at a slower rate. However, if intact conduction is present, ventricular sensing must be confirmed under the planned test conditions before the test can be performed. Therefore, the method enters a subroutine block 760 wherein ventricular sensing is reassessed as will be described below with reference to FIG. 12.

Once ventricular sensing has been reassessed, a determination is made if this test is successful, as represented by a decision block 770. If the test is not successful, then the method enters the subroutine block 740 to test ventricular sensing at a slower rate. However, if the test is determined to be successful within the decision block 770, then, as represented by a decision block 775, the method adjusts the ventricular sensitivity of the pacemaker 110 until a ventricular sensitivity threshold is identified. Once the ventricular sensitivity threshold is identified, then, as represented by a decision block 777, the ventricular sensitivity of the pacemaker 110 is set to a prescribed or programmed safety margin value above the ventricular sensitivity threshold. As used herein, sensitivity setting refers to the setting of the pacemaker 110 that defines the lowest amplitude signal that can be sensed. Sensitivity or sensing threshold, whether ventricular or atrial, refers to the most reliable (or lowest) sensitivity setting at which all signals are sensed. Sensitivity or sensing safety margin refers to the ratio of the sensing threshold over a programmed sensitivity value.

Thereafter, and as represented by a subroutine block 780, an automatic sense test is carried out, at the optimal AV delay, for patients with intact conduction. The loss of sensing is recognized by the continued presence of an R wave on the surface ECG and ventricular IEGM, together with the loss of an R wave marker and the presence of a ventricular stimulation marker.

Upon completion of the automatic sense test at block 780, the AV delay is reset or restored to a base AV delay value in use before the initialization of the test at block 700, as illustrated by an activity block 785. In addition, the PVARP is also reset or restored to a base value in use before the initialization of the test at block 700, as illustrated by an activity block 787.

When the automatic sense test has been performed at block 780 and the AV delay and PVARP values reset at blocks 785 and 787, respectively, or when testing has been conducted at a slower rate at block 740, the method for verifying or determining ventricular sensitivity terminates, as represented by an end block 790.

Figure 10A:
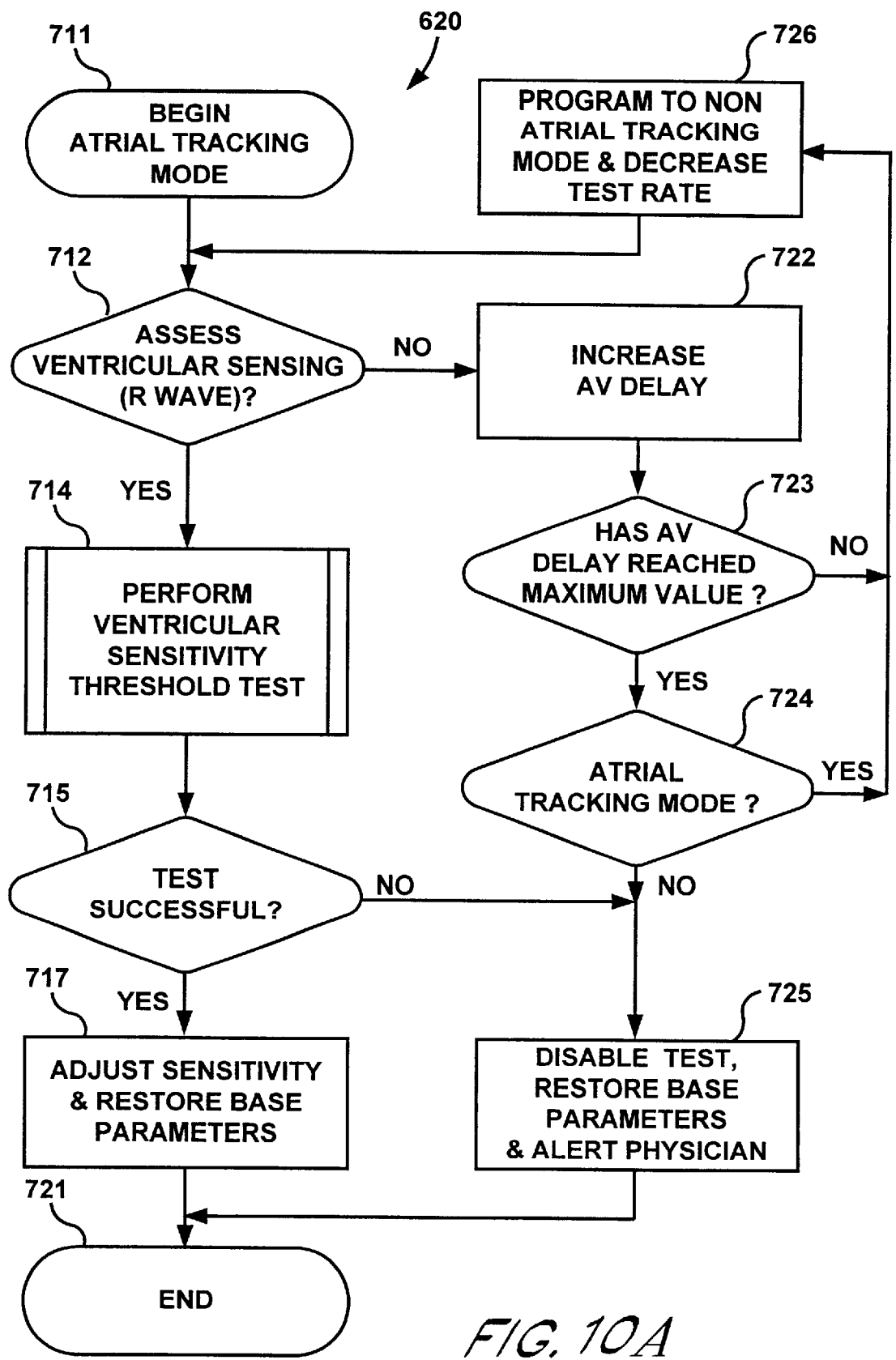
FIG. 10A is a flowchart which illustrates an alternative method employed within the subroutine block of FIG. 9 to determine the ventricular sensitivity threshold of the cardiac stimulation device.

FIG. 10A illustrates an alternative method employed within the subroutine block 620 of FIG. 9 to determine the ventricular sensitivity threshold of the pacemaker 110. The ventricular sensitivity threshold method initiates as represented by a begin block 711, and the pacemaker 110 is set to an atrial tracking mode, for example a DDD mode.

Ventricular sensing is assessed as represented by a decision block 712 for determining the presence or absence of intrinsic ventricular events. An exemplary method by which ventricular sensing is assessed will be described below with reference to FIG. 12.

If ventricular sensing is confirmed so that the pacemaker 110 accurately senses each of the significant intrinsic ventricular events within the patient's heart 115, and the method enters a subroutine block 714.

At subroutine block 714 the method can optionally, but not necessarily increase the PVARP to prevent the initiation of PMT during the performance of the atrial sensitivity threshold test. The pacemaker 110 performs a ventricular sensitivity threshold test to determine the ventricular sensitivity threshold, as described herein.

The method then determines at block 715 whether the ventricular sensitivity threshold test is successful. If this test is determined to be successful, then, as illustrated by block 717, the ventricular sensitivity of the pacemaker 110 can be automatically set or adjusted to a prescribed or programmed safety margin value from the ventricular sensitivity threshold. Alternatively, the programmer 120 recommends a ventricular sensitivity setting to the clinician 102.

Simultaneously with, or upon completion of the ventricular sensitivity threshold adjustment, the remaining parameters that have been changed for the purpose of conducting the ventricular sensitivity threshold test are also restored at block 717 to their base values prior to the initialization of the test at block 711. As an example, the pacing mode is reset to its original setting, such as the non-atrial tracking mode. The method for determining the ventricular sensitivity threshold terminates, as represented by an end block 721.

If at block 712 the ventricular sensing test is determined to be unsuccessful, so that the pacemaker 110 does not accurately sense each of the significant ventricular events within the patient's heart 115, the method proceeds to automatically adjust the AV delay by increasing it to a programmed or predetermined value, as illustrated by block 722.

The method then proceeds to a decision block 723, and inquires whether a maximum AV delay value has been reached. If the maximum AV delay value has not been reached, the method loops back to decision block 712 for reassessing the ventricular sensing. If during the ventricular assessment test at block 712, intrinsic ventricular events are not detected, the method increases the AV delay at block 722, and inquires at decision block 723 whether the maximum AV delay value has been reached. The method repeats this loop (i.e., decision block 712, activity block 722, and decision block 723), until either the ventricular sensing test at 712 is determined to be successful and the method proceeds to subroutine block 714 as describes above, or until the adjusted AV delay has reached its maximum allowed value and the method proceeds to a decision block 724.

At decision block 724 the method inquires whether the pacemaker 110 is operating in an atrial tracking mode. If it is not, the method proceeds to an activity block 725, disables the ventricular sensitivity threshold test, restores all the parameters to their base values before the initialization of the test at block 711, and alerts the physician. The method then terminates at end block 721.

If at decision block 724 it is determined that the pacemaker 110 is operating in an atrial tracking mode, the method proceeds to an activity block 726, sets the pacemaker 110 to a non-atrial tracking mode (e.g. VVI or DDI), and decreases the test rate to a lower rate such as 30 pulses per minute. The method then proceeds to decision block 712, and therefrom progresses as described above.

If at decision block 715 the test is determined to be unsuccessful, the method proceeds to activity block 725, as described above, disables the ventricular sensitivity threshold test, restores all the parameters to their base values before the initialization of the test at block 711, and alerts the physician. The method then terminates at end block 721.

Figure 11:
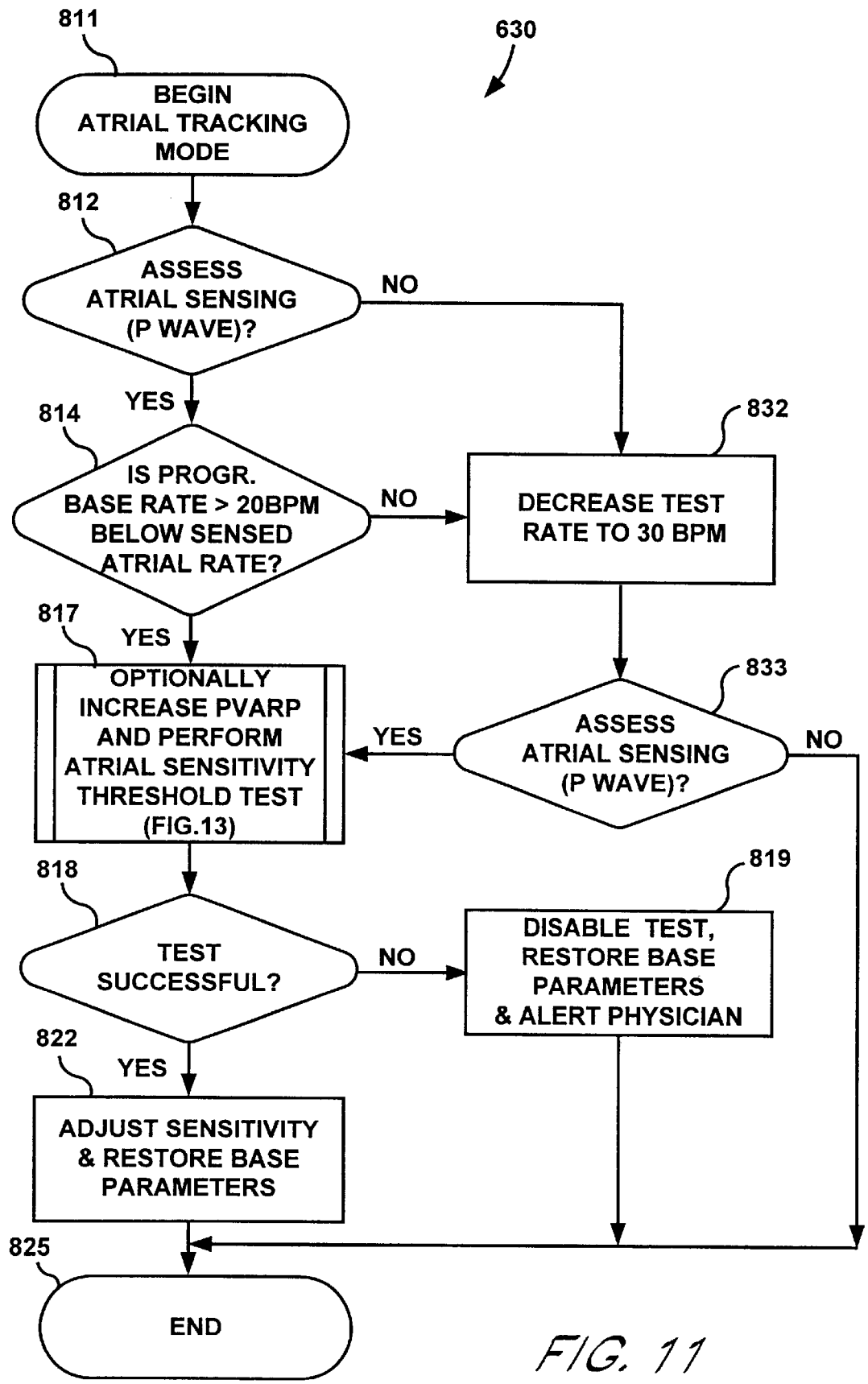
FIG. 11 is a flowchart which illustrates, in greater detail, the method employed within the subroutine block of FIG. 9 to determine the atrial sensitivity threshold of the cardiac stimulation device.

FIG. 11 illustrates a method employed within the subroutine block 630 of FIG. 9 to determine the atrial sensitivity threshold of the pacemaker 110. The atrial sensitivity threshold method initiates as represented by a begin block 811, and the pacemaker 110 is set to an atrial tracking mode, for example a DDD mode.

Atrial sensing is assessed as represented by a decision block 812 for determining the presence or absence of intrinsic atrial events. An exemplary method by which atrial sensing is assessed will be described below with reference to FIG. 13.

If atrial sensing is confirmed so that the pacemaker 110 accurately senses each of the significant intrinsic atrial events within the patient's heart 115, then the method enters a decision block 814 and determines whether the programmed base rate of the pacemaker 110 is less than the sensed atrial rate determined at decision block 812 by at least a predetermined value (for example 20 BPM). If the programmed base rate satisfies this condition, the method enters a subroutine block 817.

At subroutine block 817 the method can optionally, but not necessarily increase the PVARP to prevent the initiation of PMT during the performance of the atrial sensitivity threshold test. At subroutine block 817 the method performs an atrial sensitivity threshold test to determine the atrial sensitivity threshold, as described herein.

The method then determines at a decision block 818 whether the atrial sensitivity threshold test is successful. If this test is determined to be successful, then, as illustrated by an activity block 822, the atrial sensitivity of the pacemaker 110 can be automatically set or adjusted to a prescribed or programmed safety margin value from the atrial sensitivity threshold. Alternatively, the programmer 120 recommends an atrial sensitivity setting to the clinician 102.

Simultaneously with, or upon completion of the atrial sensitivity threshold adjustment at block 822, the remaining parameters that have been changed for the purpose of conducting the atrial sensitivity threshold test are also restored to their base values prior to the initialization of the test at block 811. As an example, the pacing mode is reset to its original setting, such as the non-atrial tracking mode. The method for determining the atrial sensitivity threshold terminates, as represented by an end block 825.

If at decision block 818 the test is determined to be unsuccessful, the method proceeds to an activity block 819, disables the atrial sensitivity threshold test, restores all the changed parameters to their base values before the initialization of the test at block 811, and alerts the physician. The method then terminates at end block 825.

If at block 812 the atrial sensing test is determined to be unsuccessful, so that the pacemaker 110 does not accurately sense each of the significant intrinsic atrial events within the patient's heart 115, the method automatically decreases the base rate to a predetermined value, for example 30 BPM, as illustrated by an activity block 832. The method employed to test atrial sensing at a slower rate will be described in greater detail below with reference to FIG. 15.

The method then enters decision block 833 and assesses atrial sensing for determining the presence or absence of intrinsic atrial events. If this test is determined to be successful, the method enters the subroutine block 817 to perform the atrial sensitivity threshold test, and therefrom progresses as described above.

If at decision block 833 the atrial sensing test is determined to be unsuccessful, the method proceeds to end block 825 and terminates the test.

If at decision block 814 the programmed base rate of the pacemaker 110 is not less than the sensed atrial rate by at least the predetermined value, the method enters activity block 832 to decrease the base rate to the predetermined value, and therefrom progresses as described above.

Figure 12:
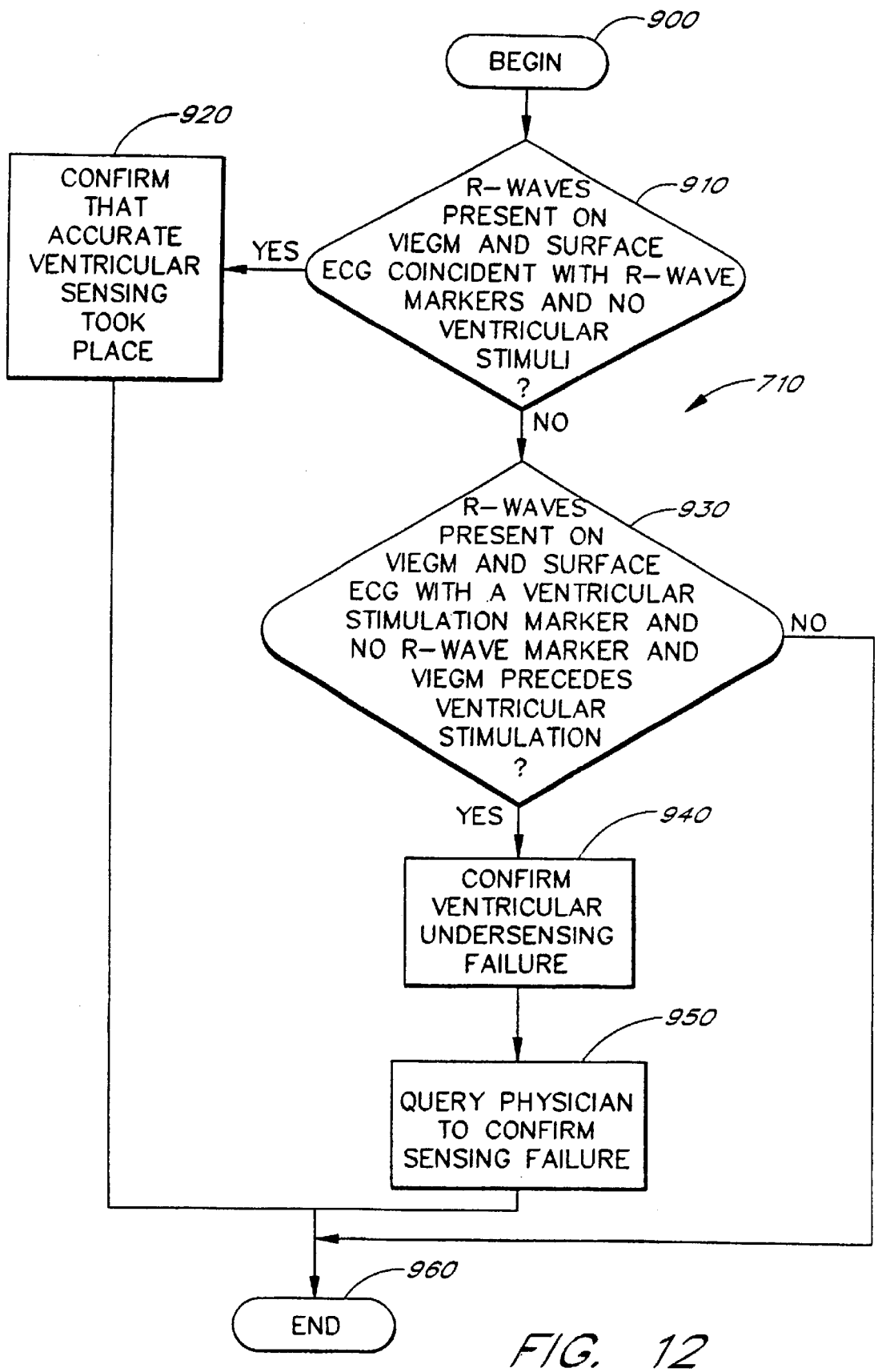
FIG. 12 is a flowchart which details the method used to assess ventricular sensing within the subroutine block of FIG. 10.

FIG. 12 is a flowchart which details the method used to assess ventricular sensing within the subroutine block 710 of FIG. 10. The method initiates as represented by a begin block 900, and thereafter a determination is made if R waves are present on the ventricular IEGM (VIEGM) and on the surface ECG coincident with R wave markers, as represented by a decision block 910. Furthermore, a determination is made if no ventricular stimuli is applied by the pacemaker 110. If the programmer 120 determines that each of these conditions is satisfied, the programmer 120 confirms that accurate ventricular sensing has taken place, as represented within an activity block 920. If these conditions are not satisfied, the programmer 120 determines if no R wave markers and VIEGM precedes the ventricular stimulation, as represented by activity block 930. If this condition is not satisfied, the sensing cannot be confirmed and the test ends, as represented by an end block 960. However, if it is determined that a ventricular stimulation marker is present and no R wave marker is present while the ventricular IEGM precedes the ventricular stimulation marker by a predetermined amount, then a ventricular undersensing failure is confirmed, as represented within an activity block 940. Once the ventricular under sensing failure has been confirmed within the activity block 940, the physician is queried to confirm the sensing failure, as represented within an activity block 950. The physician confirmation assures that no errors are made within the automatic analysis so that the monitoring physician 102 can make the final determination as to whether or not a sensing failure has taken place by observing the wave forms on the display screen 125. The method of assessing ventricular sensing terminates, as represented by an end block 960, which is entered from either the activity block 920 or the activity block 950.

Figure 13:
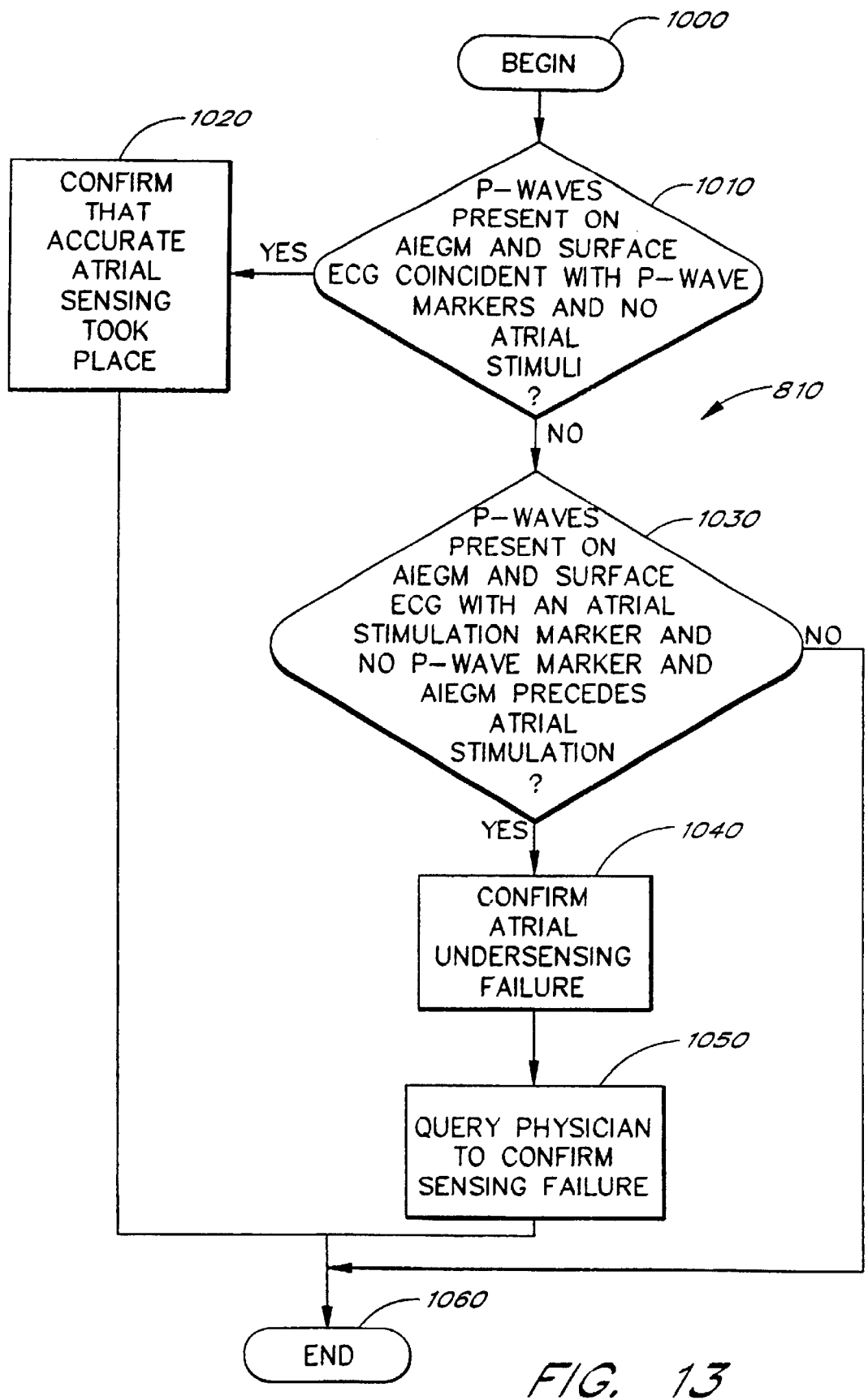
FIG. 13 is a flowchart which details the method used to assess atrial sensing within the subroutine block of FIG. 10.

FIG. 13 is a flowchart which details the method used to assess atrial sensing within block 812 of FIG. 11. The method initiates as represented by a begin block 1000, and thereafter a determination is made if P waves are present on the atrial IEGM and on the surface ECG coincident with P wave markers, as represented by a decision block 1010. Furthermore, a determination is made if no atrial stimuli is applied by the pacemaker 110. If the programmer 120 determines that each of these conditions is satisfied, the programmer 120 confirms that accurate atrial sensing has taken place, as represented within an activity block 1020. If these conditions are not satisfied, the programmer 120 determines if no P wave markers and AIEGM precedes the atrial, as represented by activity block 1030. If this condition is not satisfied, the sensing cannot be confirmed and the test ends, as represented by an end block 1060. However, if it is determined that an atrial stimulation marker is present and no P wave marker is present while the atrial IEGM precedes the atrial stimulation marker by a predetermined amount, then an atrial under sensing failure is confirmed, as represented within an activity block 1040. Once the atrial under sensing failure has been confirmed within the activity block 1040, the physician 102 is queried to confirm the sensing failure, as represented within an activity block 1050. The physician confirmation assures that no errors are made within the automatic analysis so that the monitoring physician 102 can make the final determination as to whether or not a sensing failure has taken place by observing the wave forms on the display screen 125. The method of assessing atrial sensing terminates, as represented by an end block 1060, which is entered from either the activity block 1020 or the activity block 1050.

Figure 14:
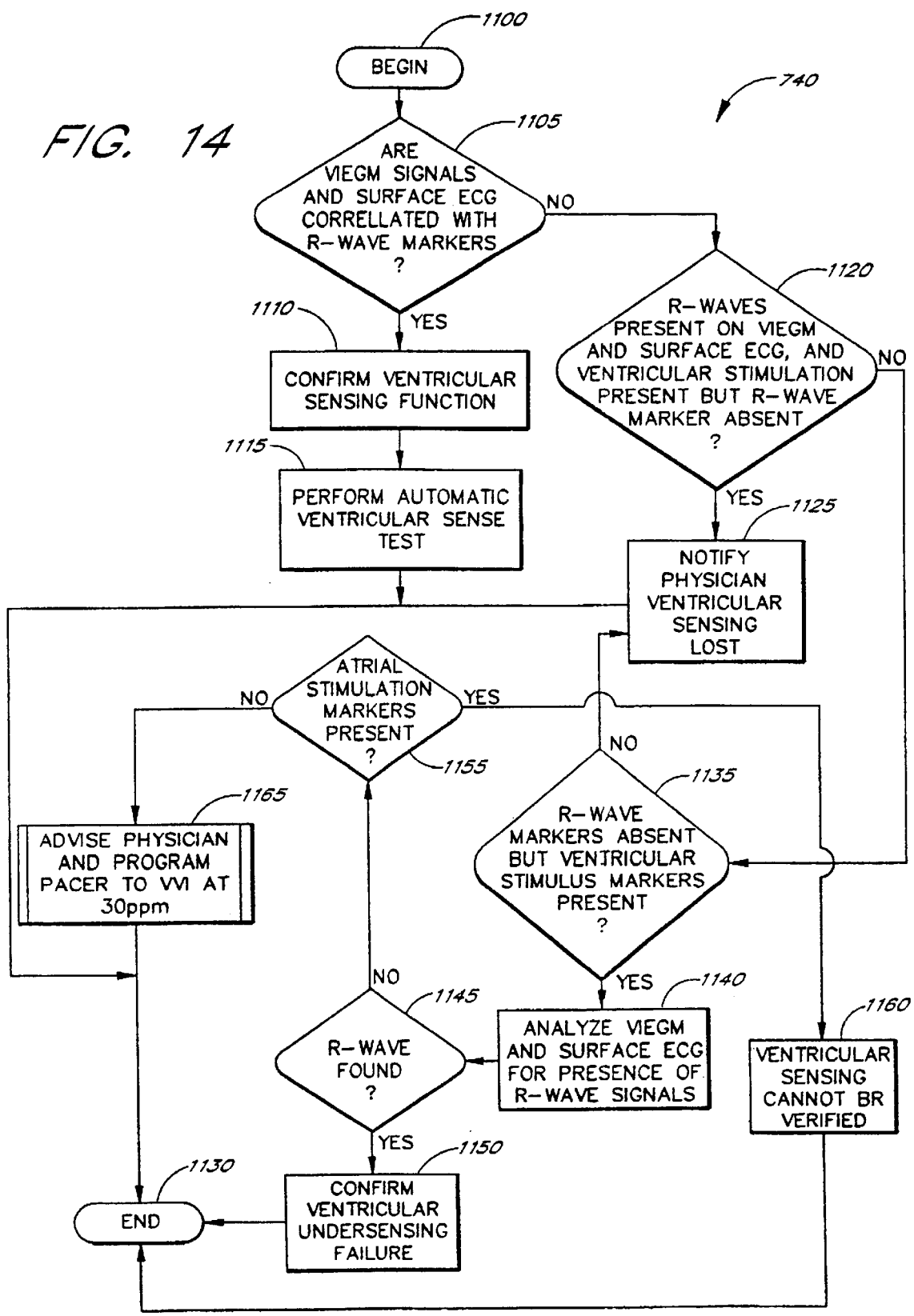
FIG. 14 is a flowchart which details the method used within the subroutine block of FIG. 10 to test ventricular sensing at a slower test rate.

FIG. 14 is a flowchart which details the method used within the subroutine block 740 of FIG. 10 to test ventricular sensing at a slower test rate (e.g., 30 pulses per minute). The method initiates as represented by a begin block 1100, and thereafter the programmer 120 determines if the ventricular IEGM signals and surface ECG signals are correlated with the R wave markers, as represented within a decision block 1105. If it is determined that the ventricular IEGM signals and the surface ECG are correlated with the R wave markers, then ventricular sensing is confirmed, as represented within an activity block 1110, and an automatic ventricular sense test is carried out, as represented within an activity block 1115.

However, if it is determined within the decision block 1105 that the ventricular IEGM signals and the surface ECG signals are not correlated with the R wave markers, then a further determination is made, as represented within a decision block 1120, if R waves are present on the ventricular IEGM and the surface ECG, and furthermore, if ventricular stimulation is present while the R wave marker is absent. If it is determined that the test conditions determined within the decision block 1120 are fulfilled, then ventricular sensing is considered to be lost, as represented within an activity block 1125, and the physician is notified via the display screen 125. However, if it is determined that the test conditions within the decision block 1120 are not met, then a still further determination is made, as represented within a decision block 1135, if R wave markers are absent but ventricular stimulus markers are present. If R wave markers are absent while the ventricular stimulus markers are present, then the ventricular IEGM and surface ECG are analyzed for the presence of R wave signals, as represented within an activity block 1140. However, if it is determined that the ventricular stimulus markers are not present or that the R wave markers are not absent, then ventricular sensing is considered to be lost and a monitoring physician 102 is notified via the display screen 125, as represented within the activity block 1125. Once ventricular sensing has been confirmed lost, the method terminates as represented within an end block 1130.

If it was determined within the decision block 1135 that R wave markers were absent but ventricular stimulus markers were present, so that the ventricular IEGM and the surface ECG were analyzed for the presence of R wave signals, then a further determination is made, as represented within a decision block 1145, if R wave markers were found during the analysis performed within the activity block 1140. If it is determined that R wave markers were found, then a ventricular under sensing failure is confirmed, as represented within an activity block 1150. However, if no R wave markers are found, a further determination is made of atrial stimulation markers are present, as represented within a decision block 1155. If it is determined that atrial stimulation markers are present, then the programmer 120 reports that ventricular sensing cannot be verified as represented within activity block 1160. However, if it is determined within the decision block 1155 that atrial stimulation markers are not present, then the physician 102 is advised of this condition and the pacemaker 110 is programmed by the programmer 120 to initiate ventricular inhibited pacing at 30 pulses per minute, as represented within a subroutine block 1165. The method employed within the subroutine block 1165 is described in greater detail below with reference to FIG. 16. The method terminates, as represented within the end block 1130, which may be entered from the subroutine block 1165, the activity block 1150, the activity block 1160, or the activity block 1125 of FIG. 14.

Figure 15:
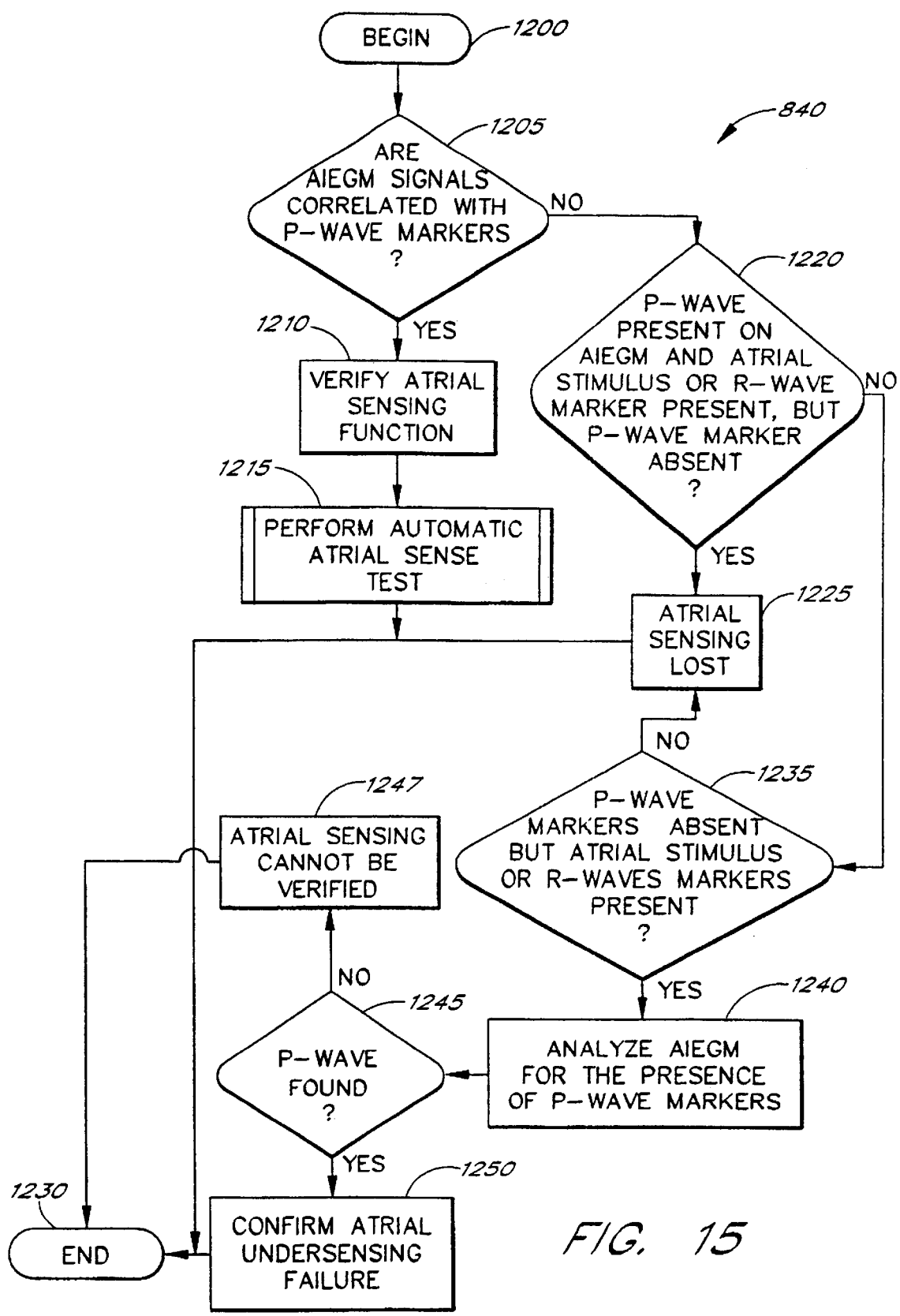
FIG. 15 is a flowchart which details the method employed within the subroutine block of FIG. 11 to atrial sensing at a slower test rate.

FIG. 15 is a flowchart which details the method employed within block 812 of FIG. 11 to test atrial sensing at a slow rate (e.g., 30 pulses per minute). The method initiates as represented by a begin block 1200, and a determination is made if the atrial IEGM (AIEGM) signals are correlated with the P wave markers, as represented within a decision block 1205. If the atrial IEGM signals are correlated with the P wave markers, then atrial sensing is verified, as represented within an activity block 1210, and an automatic atrial sense test is performed, as represented within an activity block 1215. The automatic atrial sense test will be described below in reference to FIG. 20.

If it is determined within the decision block 1205 that the atrial IEGM signals are not correlated with the P wave markers, then a further determination is made if P waves are present on the atrial IEGM and atrial stimulus markers are present, while the P wave markers are absent. This determination is represented within a decision block 1220. If the conditions within the decision block 1220 are satisfied, then the programmer 120 confirms that atrial sensing is lost and sends a message to the monitoring physician 102 via the display screen 125, as represented within an activity block 1225. However, if the test conditions within the decision block 1220 are not satisfied, then a further determination is made, as represented within decision block 1235, if the P wave markers are absent, while the atrial stimulus or the R wave markers are present for at least a predetermined time delay. If the test conditions of the decision block 1235 are not satisfied, then atrial sense is lost, and a notification is provided to the monitoring physician 102 via the display screen 125, as represented within the activity block 1225. If it is determined that atrial sensing is lost, then the method for testing atrial sensitivity terminates, as represented within an end block 1230.

However, if it is determined within the decision block 1235 that P wave markers are absent while the atrial stimulus or R wave markers were present, then the atrial IEGM is analyzed for the presence of P wave markers. If no P wave markers are found, as represented within a decision block 1245, then the programmer 120 reports that atrial sensing cannot be verified as represented within an activity block 1247. However, if it is determined that P wave markers are found within the decision block 1245, then an atrial under sensing failure is confirmed, as represented within an activity block 1250, and the monitoring physician 102 is notified of the atrial under sensing failure. The physician is then given the opportunity to confirm the atrial under sensing failures based upon the physician's observations of the displayed surface ECG and atrial IEGM. Thereafter, the method terminates within the end block 1230.

Figure 16:
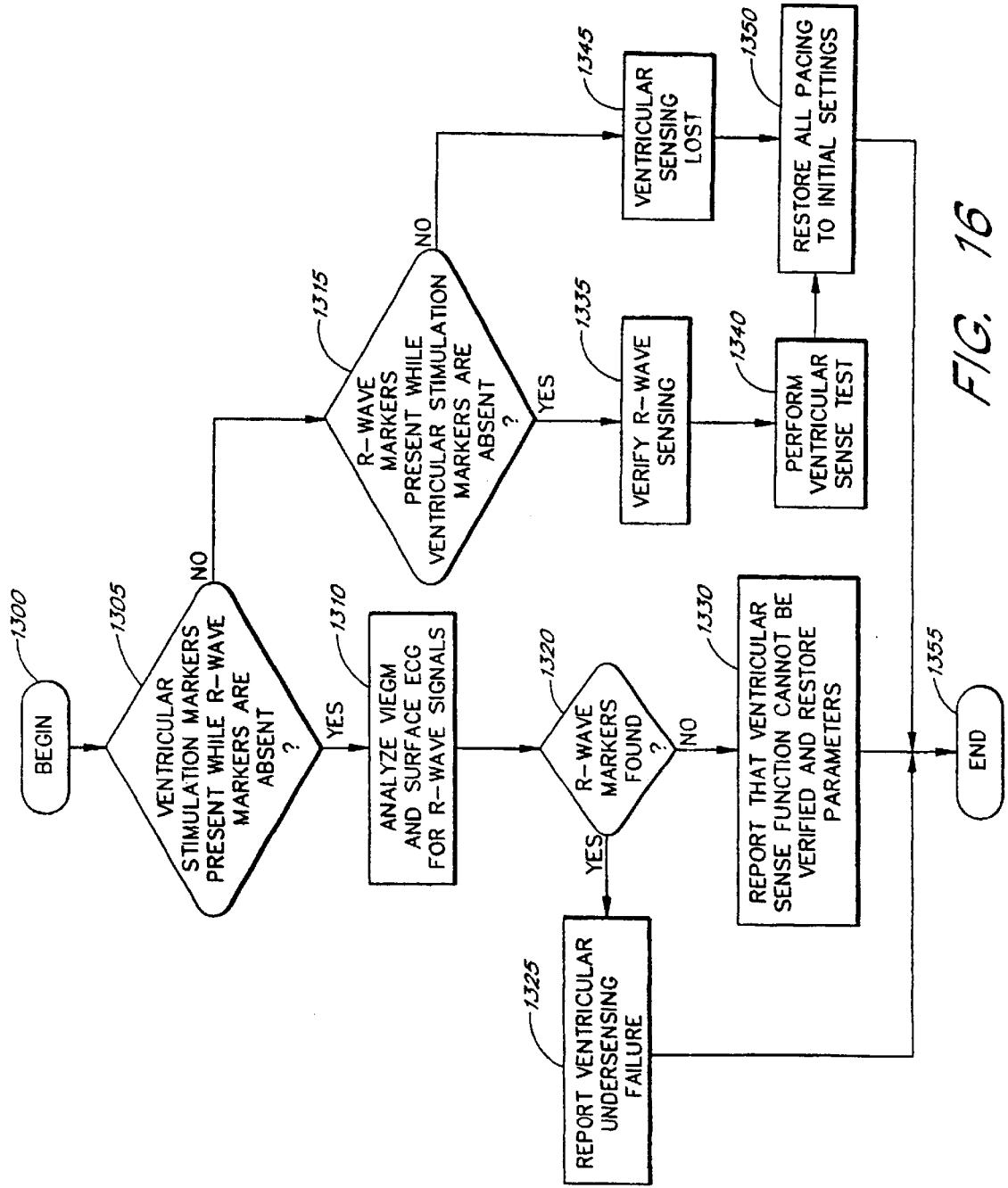
FIG. 16 is a flowchart which details the method employed within the subroutine block of FIG. 14 to program the pacemaker to perform ventricular inhibited pacing.

FIG. 16 is a flowchart which details the method employed within the subroutine block 1165 of FIG. 14 to program the pacemaker 110 to perform ventricular inhibited pacing. The method initiates as represented within a begin block 1300, and thereafter, a determination is made if ventricular stimulation markers are present, while R wave markers are absent, as represented within a decision block 1305. If ventricular stimulation markers are present while the R wave markers are absent, then the ventricular IEGM and surface ECG are analyzed for R wave signals, as represented within an activity block 1310. However, if ventricular stimulation markers are not present or the R wave markers are not absent, a further determination is made within a decision block 1315 if R wave markers are present while the ventricular stimulation markers are absent.

If during the analysis of the ventricular IEGM and surface ECG 1310, R wave markers are found, as represented within a decision block 1320, then a ventricular under sensing failure is reported to the monitoring physician 102 via the display screen 125, as represented within an activity block 1325. However, if no R wave markers are found upon the analysis, then the programmer 120 reports that ventricular sensing cannot be verified, and the programmer 120 restores the parameters of the pacemaker 110 to their original settings, as represented within an activity block 1330. Thereafter, the method terminates from the activity blocks 1325 or 1330, as represented by an end block 1355.

Within the decision block 1350, if it is determined that R waves are present while ventricular stimulation markers are absent, then the R wave sensing is verified, as represented within an activity block 1335, and a ventricular sense test is performed automatically, as represented within an activity block 1340. It should be noted that the ventricular sense test performed within the activity block 1340 is performed at a slow rate of 30 pulses per minute. However, if it was determined within the decision block 1315 that either the R waves are absent or the ventricular stimulation markers were present, then the programmer 120 reports that ventricular sensing has been lost, as represented within an activity block 1345, and all pacing values are restored to their initial settings by the programmer 120, as represented within an activity block 1350. The activity block 1350 is entered from either the activity block 1340 or the activity block 1345. The method for testing ventricular sensing in the ventricular-inhibited pacing mode terminates within the end block 1355.

Figure 17:
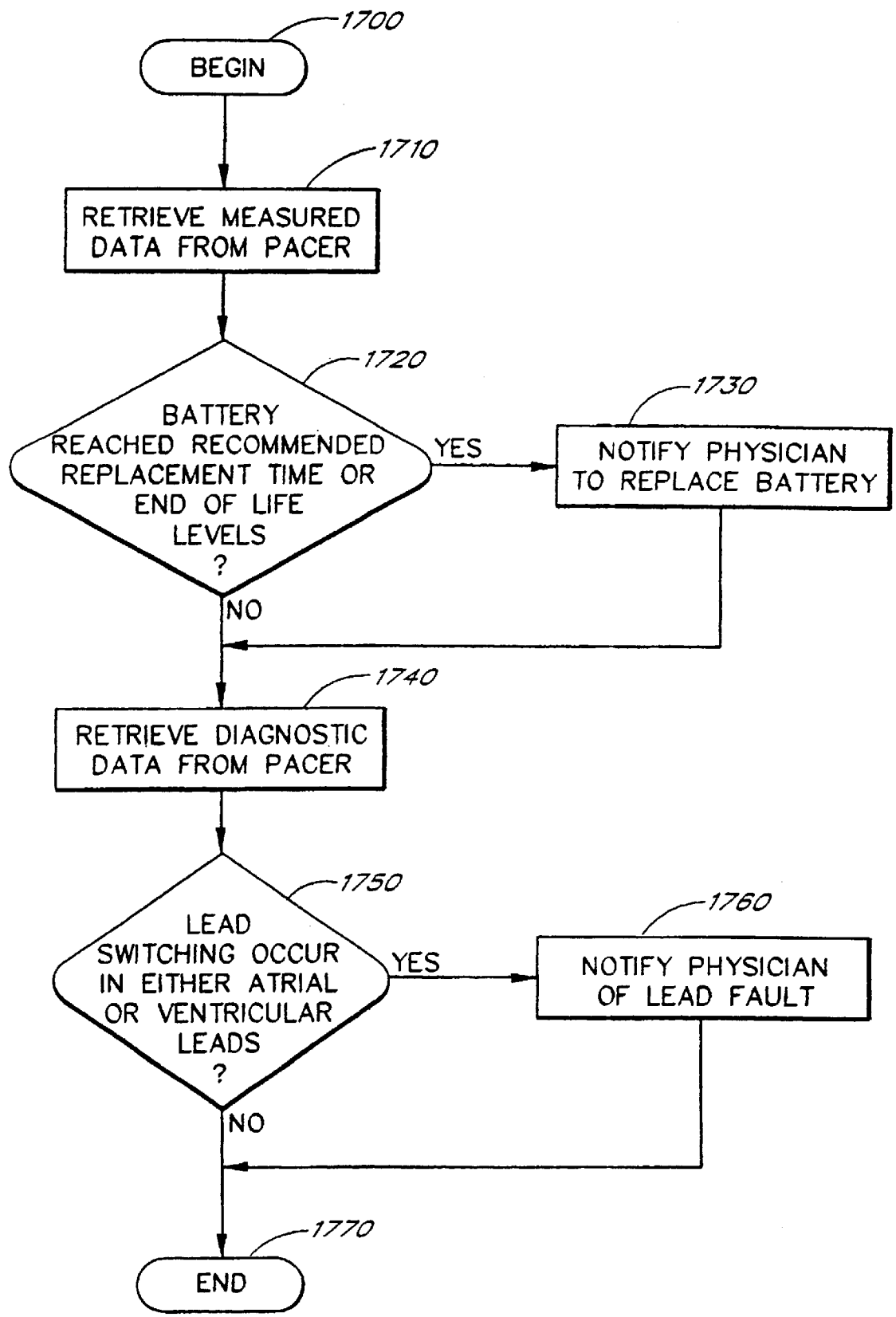
FIG. 17 is a flowchart which details the method used within the subroutine block of FIG. 7 to test the battery and leads.

FIG. 17 is a flowchart which details the method employed within the subroutine block 430 of FIG. 7 to test the battery and leads. The test initiates as represented within a begin block 1700, and thereafter, the measured data is retrieved from the pacemaker (if not yet retrieved), as represented within an activity block 1710. From the measured data, the Daily Average Battery Voltage is analyzed to determine if the battery has reached the Recommended Replacement Time or End of Life levels, as represented within a decision block 1720. If either of these conditions is met, the programmer 120 notifies the physician of the need to replace the battery, as represented within an activity block 1730. If neither condition is met, the battery is determined to be operating within acceptable parameters. At this point, the battery test is complete and the lead tests begin.

To perform the lead tests, diagnostic data is retrieved from the pacemaker, as represented within an activity block 1740. From the diagnostic data, the status bits of a lead supervision algorithm are analyzed to determine if lead switching was performed in either the atrial or ventricular leads, as represented within a decision block 1750. As used herein, lead supervision relates to the measurement of lead impedance and possibly the determination of the lead tip or electrode polarities based on whether the impedance is within a predefined range. If lead switching has occurred, the physician is notified of a lead fault, as represented within an activity block 1760. If no lead switching has occurred, the leads are determined to be operating normally. The battery and lead test then terminates within the end block 1770.

Figure 18:
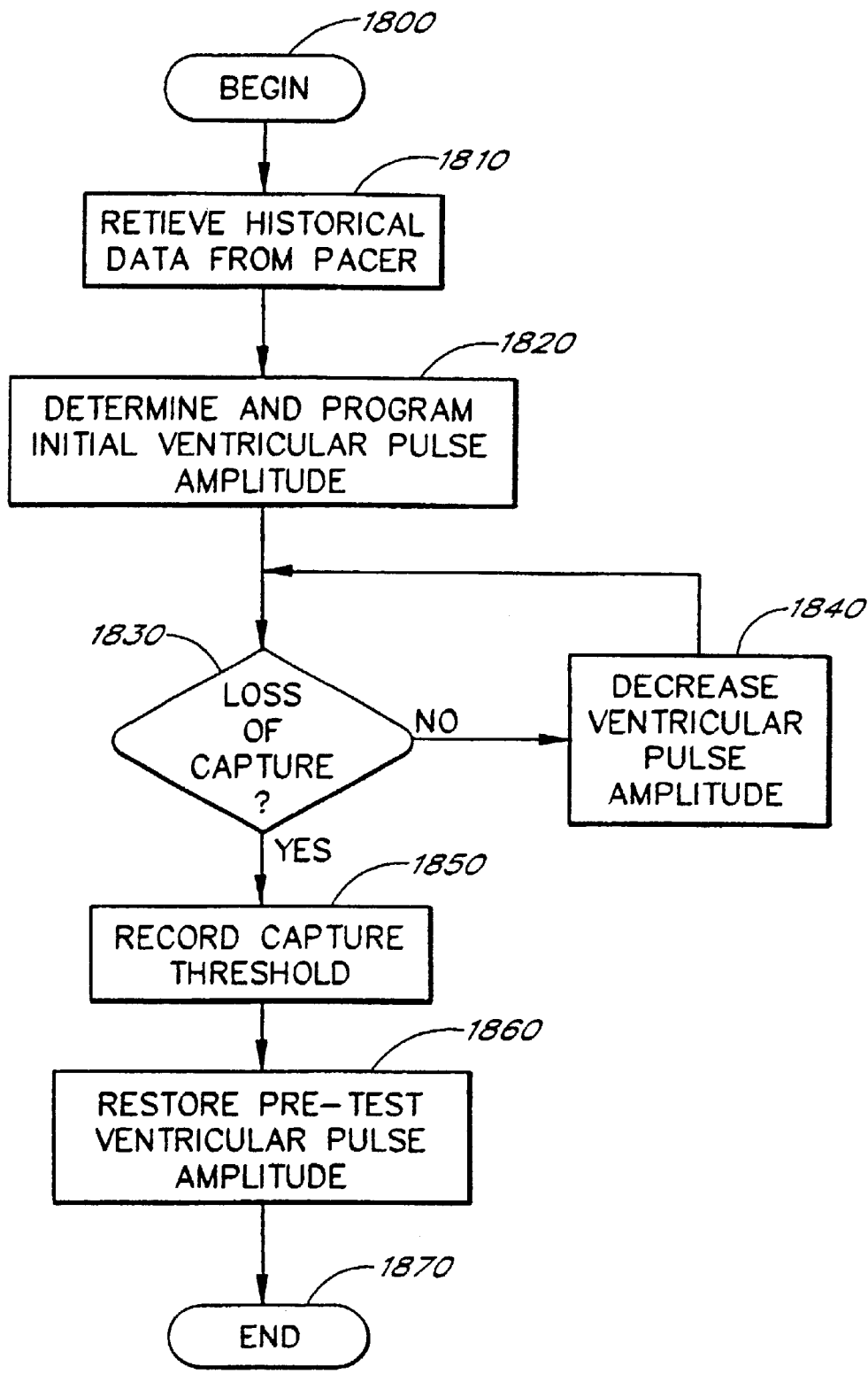
FIG. 18 is a flowchart which details the method employed within the subroutine block of FIG. 8 to test the ventricular capture function.

FIG. 18 is a flowchart which details the method employed within the subroutine blocks 477 and 480 of FIG. 8 to perform a ventricular capture test. The test initiates as represented by a begin block 1800 and then historical data is retrieved from the pacemaker as indicated within an activity block 1810. From the historical data, an initial ventricular pulse amplitude is determined and programmed into the pacemaker, as represented within activity block 1820.

Typically, the initial pulse amplitudes is one increment below the currently programmed amplitude. However, a preferred embodiment of the present invention uses the historical data to estimate the amplitude at which capture will be lost. Then, the amplitude step immediately above that estimated value is used as the initial value. This reduces the number of amplitude steps which must be programmed during the test.

The test then determines if loss of capture occurs, as represented within decision block 1830. Loss of capture is declared when no ventricular event is detected in the ECG waveform during the 120 ms following a "V" marker.

If loss of capture is not detected, the ventricular pulse amplitude is decreased as represented within activity block 1840. The amplitude is decreased until loss of capture is detected.

When loss of capture is detected, the programmer 120 records the capture threshold as represented within activity block 1850. The ventricular pulse amplitude is restored to the pre-test value, as represented within activity block 1860 and the test terminates in the end block 1870.

Figure 19:
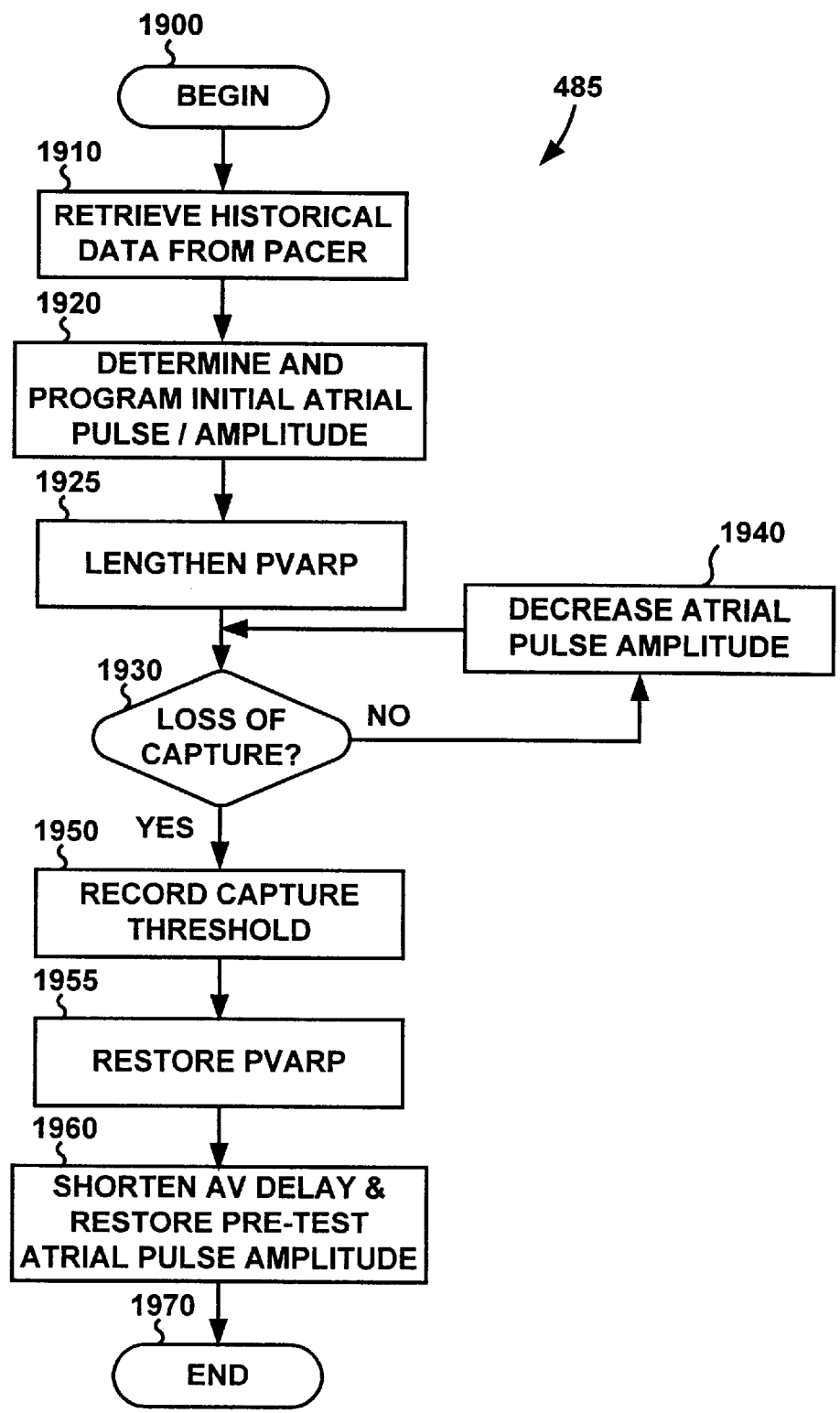
FIG. 19 is a flowchart which details the method employed within the subroutine block of FIG. 8 for determining atrial autocapture using a programmable AV delay.

FIG. 19 is a flowchart which details the method employed within the subroutine block 485 of FIG. 8 to perform an atrial capture test. The test initiates as represented by a begin block 1900 and then historical data is retrieved from the pacemaker as indicated within an activity block 1910. From the historical data, an initial atrial pulse amplitude is determined and programmed into the pacemaker 110, as represented by an activity block 1920.

Typically, the initial pulse amplitude is one increment below the currently programmed amplitude. However, a preferred embodiment of the present invention uses the historical data to estimate the amplitude at which capture will be lost. Then, the amplitude step immediately above the estimated value is used as the initial value. This reduces the number of amplitude steps that are programmed during the test. While atrial stimulation pulses are generated, the ventricular stimulation pulses can be maintained at a level known to ensure capture in the ventricle.

As it will be explained later in greater detail, the pacemaker 110 includes a processor, and timing and control circuits 2286 (FIG. 22) configured to control various timing intervals including the AV delay and the PVARP. The pacemaker 110 lengthens the post-ventricular refractory period (PVARP) as illustrated by an activity block 1925, to reduce the possibility of premature and retrograde P-waves being detected as true cardiac contractions. The lengthening of the PVARP can be accomplished either gradually in incremental steps, or programmably to a preset value.

The test then determines if loss of capture occurs, as represented by a decision block 1930. Loss of capture is declared in one of two situations. If intact conduction is present and the pre-test rhythm was AR, then loss of capture is declared when the "A" marker is followed by a "V" marker instead of an "R" marker. Alternatively, loss of capture is declared if no atrial event is detected in the ECG waveform during the 120 ms following an "A" marker.

If loss of capture is not detected, the processor 2286 triggers the atrial pulse generator 2278 to decrease the atrial pulse amplitude as represented by an activity block 1940, until loss of capture is detected.

In response to the detection of loss of capture, a memory 2300 (FIG. 22) records the capture threshold as represented by an activity block 1950. The PVARP is restored to its base or pre-test value, as illustrated by an activity block 1955.

As illustrated by an activity block 1960, in response to the loss of capture, the processor 2286 automatically shortens the AV delay, substantially or sufficiently, in order to reduce the possibility of a retrograde P-wave initiating a pacemaker-mediated tachycardia, and restores the atrial pulse amplitude to its pre-test value or to a value above the atrial capture threshold, or within a safety margin from the atrial capture threshold. The test terminates at an end block 1970.

Figure 19A:
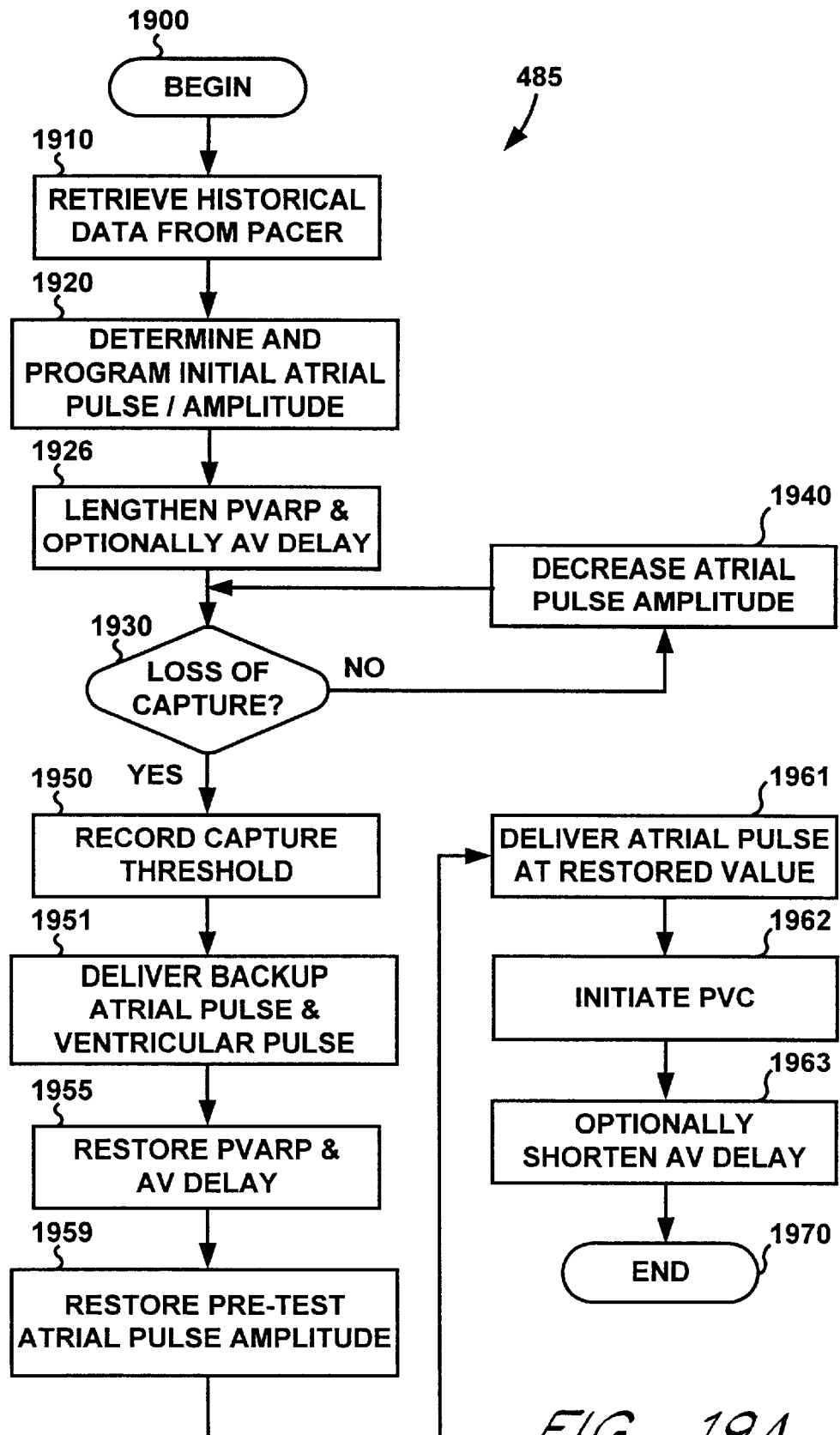
FIG. 19A is a flowchart which details the method employed within the subroutine block of FIG. 8 for determining atrial autocapture using a programmable PVARP.

FIG. 19A is a flowchart which details the method employed within the subroutine block 485 of FIG. 8 to perform an atrial capture test. The test initiates as represented by a begin block 1900 and then historical data is retrieved from the pacemaker as indicated within an activity block 1910. From the historical data, an initial atrial pulse amplitude is determined and programmed into the pacemaker 110, as represented by an activity block 1920.

Typically, the initial pulse amplitude is one increment below the currently programmed amplitude. However, a preferred embodiment of the present invention uses the historical data to estimate the amplitude at which capture will be lost. Then, the amplitude step immediately above the estimated value is used as the initial value. This reduces the number of amplitude steps that are programmed during the test. While atrial stimulation pulses are generated, the ventricular stimulation pulses can be maintained at a level known to ensure capture in the ventricle.

The pacemaker 110 automatically lengthens the post-ventricular refractory period (PVARP) from a first (or base) value to a second value, as illustrated by an activity block 1926, to reduce the possibility of premature and retrograde P-waves being detected as true cardiac contractions. The lengthening of the PVARP can be accomplished either gradually in incremental steps, or programmably to a preset value. Optionally, the pacemaker 110 automatically lengthens the AV delay from a first (or base) value to a second value, such that the atrial capture test can be performed at a slightly reduced ventricular rate without potentially inducing a temporary bradycardic rhythm.

The test then determines if loss of capture occurs, as represented by a decision block 1930. Loss of capture is declared in one of two situations. If intact conduction is present and the pre-test rhythm was AR, then loss of capture is declared when the "A" marker is followed by a "V"

marker instead of an "R" marker. Alternatively, loss of capture is declared if no atrial event is detected in the ECG waveform during the 120 ms following an "A" marker. Optionally, a marker channel is generated to indicate the atrial stimulation pulse timing, and the marker channel is compared to the ECG signal.

If loss of capture is not detected, the processor 2286 (FIG. 22) triggers the atrial pulse generator 2278 (FIG. 22) to decrease the atrial pulse amplitude as represented by an activity block 1940, until loss of capture is detected. When loss of capture is detected, the memory 2300 (FIG. 22) records the capture threshold as represented by an activity block 1950.

In response to loss of capture, and as illustrated by an activity block 1951, the processor 2286 triggers the atrial pulse generator 2278 to deliver a backup atrial stimulation pulse concurrently with a ventricular stimulation pulse, such that the possibility of a retrograde P-wave initiating a pacemaker-mediated tachycardia (PMT) is further minimized since the atrial tissue becomes refractory due to the backup atrial stimulation pulse. The PVARP and AV delay are restored to their respective first values, as illustrated by an activity block 1955.

As illustrated by an activity block 1959, the processor 2286 restores the atrial pulse amplitude to its pre-test value or to a value above the atrial capture threshold, or within a safety margin from the atrial capture threshold. The processor 2286 then triggers the atrial pulse generator 2278 to deliver an atrial stimulation pulse having the restored value in a subsequent cardiac cycle as illustrated by an activity block 1961, and automatically initiates a premature ventricular contraction (PVC) response algorithm to prevent a retrograde P-wave from starting a PMT as illustrated by an activity block 1962, so that the possibility of a retrograde P-wave initiating a PMT is reduced.

Optionally, the processor 2286 can trigger the atrial pulse generator 2278 to generate an atrial stimulation pulse having the restored value in a subsequent cardiac cycle as illustrated by an activity block 1961, and can substantially shorten the AV delay as illustrated by an activity block 1963, so that the possibility of a retrograde P-wave initiating a PMT is reduced. The test terminates at an end block 1970.

Figure 19B:
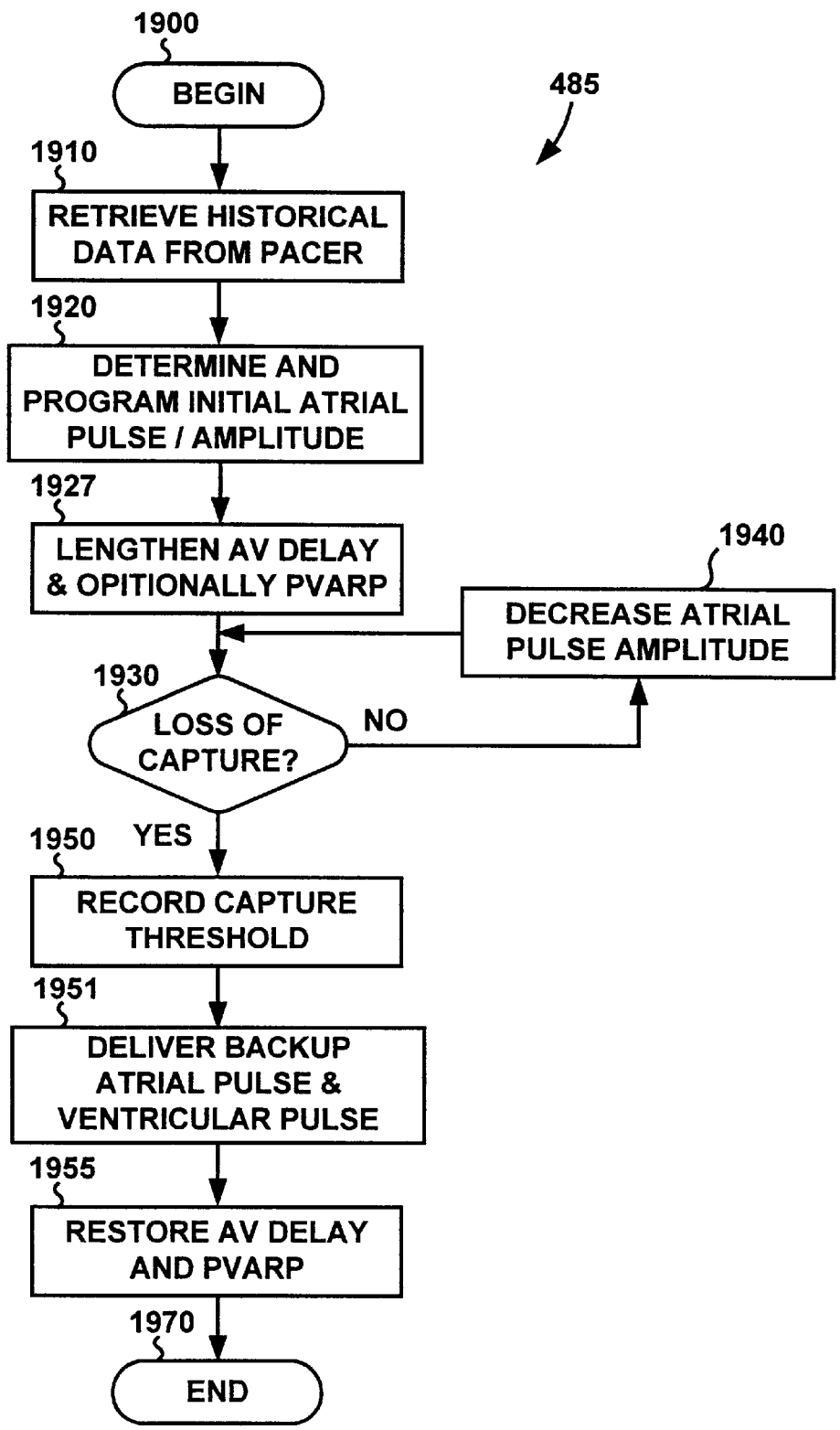
FIG. 19B is a flowchart which details the method employed within the subroutine block of FIG. 8 for determining atrial autocapture using a backup atrial stimulation.

FIG. 19B is a flowchart which details the method employed within the subroutine block 485 of FIG. 8 to perform an atrial capture test. The test initiates as represented by a begin block 1900 and then historical data is retrieved from the pacemaker as indicated within an activity block 1910. From the historical data, an initial atrial pulse amplitude is determined and programmed into the pacemaker 110, as represented by an activity block 1920.

Typically, the initial pulse amplitude is one increment below the currently programmed amplitude. However, a preferred embodiment of the present invention uses the historical data to estimate the amplitude at which capture will be lost. Then, the amplitude step immediately above the estimated value is used as the initial value. This reduces the number of amplitude steps that are programmed during the test. While atrial stimulation pulses are generated, the ventricular stimulation pulses can be maintained at a level known to ensure capture in the ventricle.

The pacemaker 110 automatically lengthens the AV delay from a first (or base) value to a second value, as illustrated by an activity block 1927. Optionally, the pacemaker 110 automatically lengthens the post-ventricular refractory period (PVARP) from a first (or base) value to a second value in order to reduce the possibility of premature and retrograde P-waves being detected as true cardiac contractions. The lengthening of the PVARP can be accomplished either gradually in incremental steps, or programmably to a preset value.

The test then determines if loss of capture occurs, as represented by a decision block 1930. Loss of capture is declared in one of two situations. If intact conduction is present and the pre-test rhythm was AR, then loss of capture is declared when the "A" marker is followed by a "V" marker instead of an "R" marker. Alternatively, loss of capture is declared if no atrial event is detected in the ECG waveform during the 120 ms following an "A" marker. Optionally, a marker channel is generated to indicate the atrial stimulation pulse timing, and the marker channel is compared to the ECG signal.

If loss of capture is not detected, the processor 2286 (FIG. 22) triggers the atrial pulse generator 2278 (FIG. 22) to decrease the atrial pulse amplitude as represented by an activity block 1940, until loss of capture is detected. When loss of capture is detected, the memory 2300 (FIG. 22) records the capture threshold as represented by an activity block 1950.

In response to loss of capture, and as illustrated by an activity block 1951, the processor 2286 triggers the atrial pulse generator 2278 to deliver a backup atrial stimulation pulse concurrently with a ventricular stimulation pulse, such that the possibility of a retrograde P-wave initiating a pacemaker-mediated tachycardia (PMT) is further minimized since the atrial tissue becomes refractory due to the backup atrial stimulation pulse. The AV delay and PVARP are restored to their respective first values, as illustrated by an activity block 1955. The test terminates at an end block 1970.

Figure 19C:
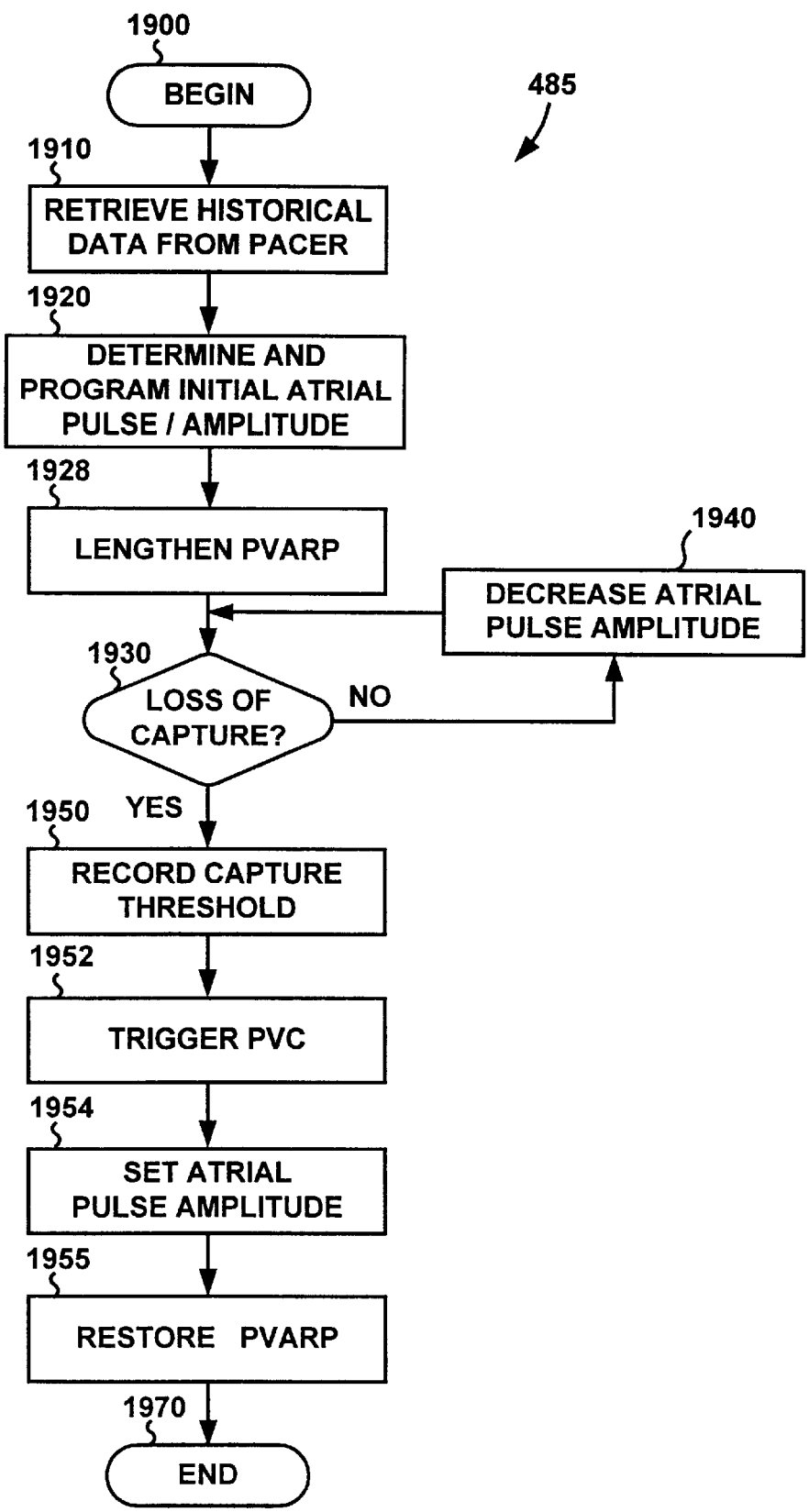
FIG. 19C is a flowchart which details the method employed within the subroutine block of FIG. 8 for determining atrial autocapture using a PVC response.

FIG. 19C is a flowchart which details the method employed within the subroutine block 485 of FIG. 8 to perform an atrial capture test. The test initiates as represented by a begin block 1900 and then historical data is retrieved from the pacemaker as indicated within an activity block 1910. From the historical data, an initial atrial pulse amplitude is determined and programmed into the pacemaker 110, as represented by an activity block 1920.

Typically, the initial pulse amplitude is one increment below the currently programmed amplitude. However, a preferred embodiment of the present invention uses the historical data to estimate the amplitude at which capture will be lost. Then, the amplitude step immediately above the estimated value is used as the initial value. This reduces the number of amplitude steps that are programmed during the test. While atrial stimulation pulses are generated, the ventricular stimulation pulses can be maintained at a level known to ensure capture in the ventricle.

The pacemaker 110 automatically lengthens the post-ventricular refractory period (PVARP) from a first (or base) value to a second value in order to reduce the possibility of premature and retrograde P-waves being detected as true cardiac contractions. The lengthening of the PVARP can be accomplished either gradually in incremental steps, or programmably to a preset value.

The test then determines if loss of capture occurs, as represented by a decision block 1930. Loss of capture is declared in one of two situations. If intact conduction is present and the pre-test rhythm was AR, then loss of capture is declared when the "A" marker is followed by a "V" marker instead of an "R" marker. Alternatively, loss of capture is declared if no atrial event is detected in the ECG waveform during the 120 ms following an "A" marker. Optionally, a marker channel is generated to indicate the atrial stimulation pulse timing, and the marker channel is compared to the ECG signal.

If loss of capture is not detected, the processor 2286 (FIG. 22) triggers the atrial pulse generator 2278 (FIG. 22) to decrease the atrial pulse amplitude as represented by an activity block 1940, until loss of capture is detected. When loss of capture is detected, the memory 2300 (FIG. 22) records the capture threshold as represented by an activity block 1950.

In response to loss of capture, and as illustrated by an activity block 1952, the processor 2286 automatically triggers a premature ventricular contraction (PVC) response to prevent a retrograde P-wave from starting a pacemaker-mediated tachycardia. A PVC is a ventricular contraction that occurs out of sequence, i.e., after a previous ventricular contraction but prior to a succeeding atrial contraction. Reference is made to U.S. Pat. Nos. 4,788,980 and 5,097,832, both of which are incorporated herein by reference.

In response to loss of atrial capture, the processor 2286 sets the atrial stimulation pulse amplitude to a value above the atrial threshold in a subsequent cardiac cycle as illustrated by an activity block 1954. Also in response to loss of atrial capture, the processor 2286 restores the PVARP to its first value as illustrated by a block 1956. The test terminates at an end block 1970.

Figure 20:
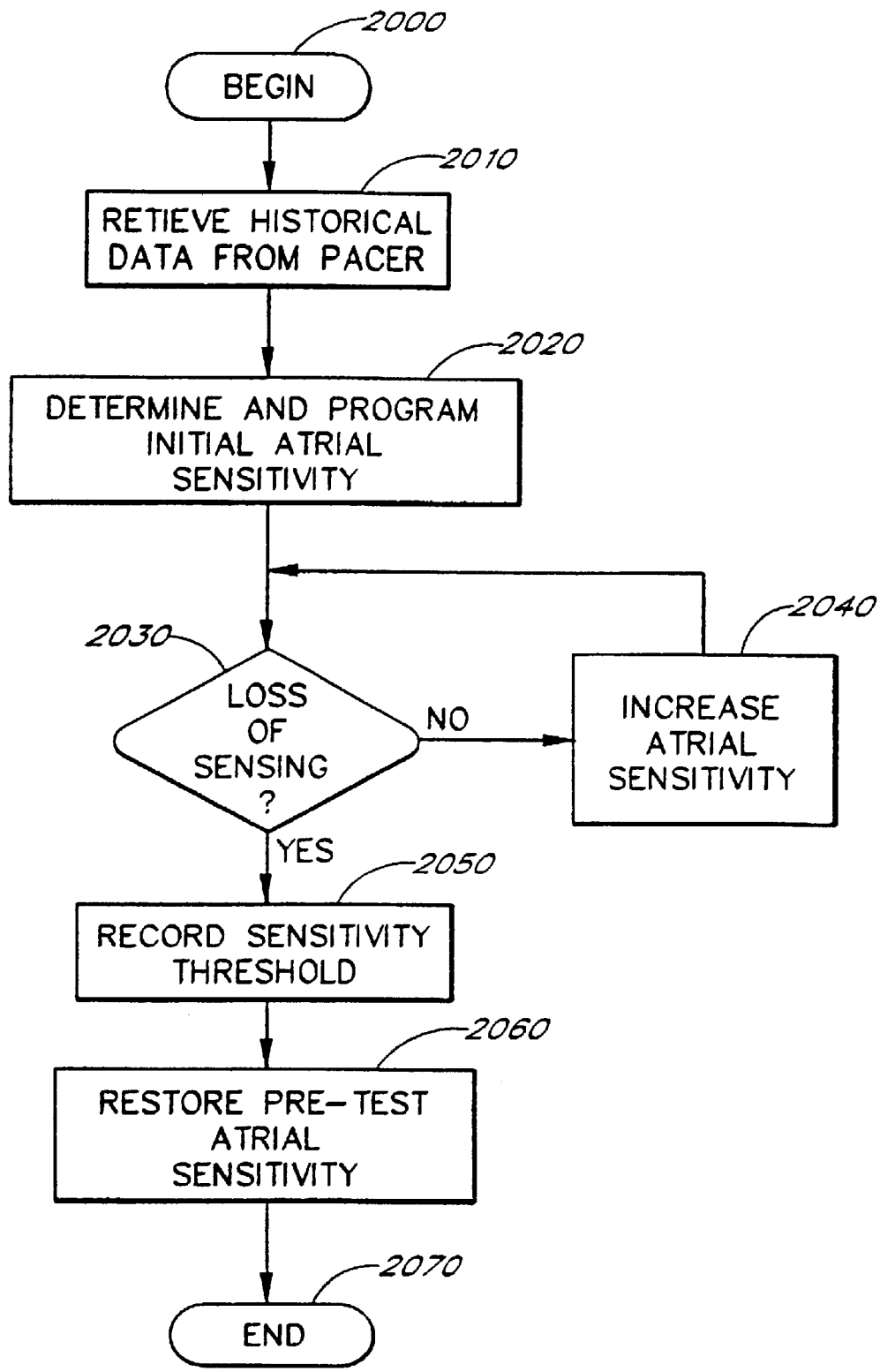
FIG. 20 is a flowchart which details the method employed within the subroutine block of FIG. 15 to test atrial sensitivity.

FIG. 20 is a flowchart which details the method employed within the subroutine block 1215 of FIG. 15 to perform an automatic atrial sense test. The test initiates as represented by a begin block 2000 and then historical data is retrieved (if not yet retrieved) from the pacemaker as indicated within an activity block 2010. From the historical data, an initial atrial sensitivity is determined and programmed into the pacemaker, as represented within activity block 2020. The sensitivity step immediately below the value in the historical data at which sensitivity is lost is used as the initial value. The test then determines if a loss of sensing occurs, as represented within decision block 2030. A loss of sensing is declared if a P-wave is detected in the IEGM waveform, followed by an "A" marker or "R" marker, and no "P" marker. If a loss of sensing is not detected, the atrial sensitivity is increased as represented within activity block 2040. The sensitivity is increased until a loss of sensing is detected. After a loss of sensing is detected, the programmer 120 records the sensitivity threshold as represented within activity block 2050. The atrial sensitivity is restored to the pre-test value, as represented within activity block 2060 and the test terminates in the end block 2070.

Automating the above tests as described above significantly shortens the time required to perform the follow-up examination. For example, the follow-up time for a complex DDD pacer could be shortened from more than 15 minutes to less than 2 minutes. Of course, while a DDD follow-up is detailed herein, similar analysis may be performed for other pacing systems.

Figure 21:
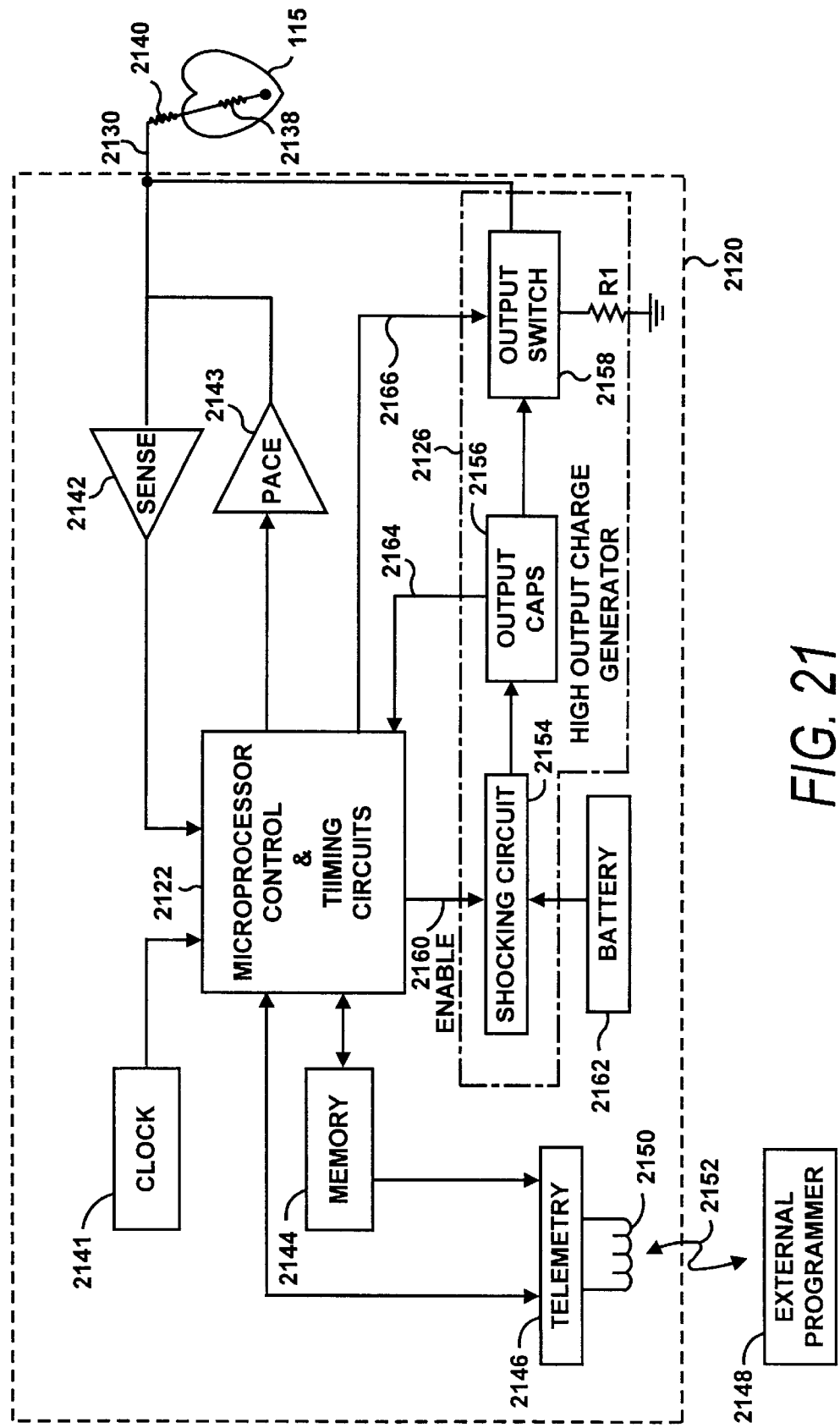
FIG. 21 shows a simplified functional block diagram of an implantable cardioverter-defibrillator (ICD), which represents one type of implantable stimulation device with which the present invention may be used.
Figure 22:
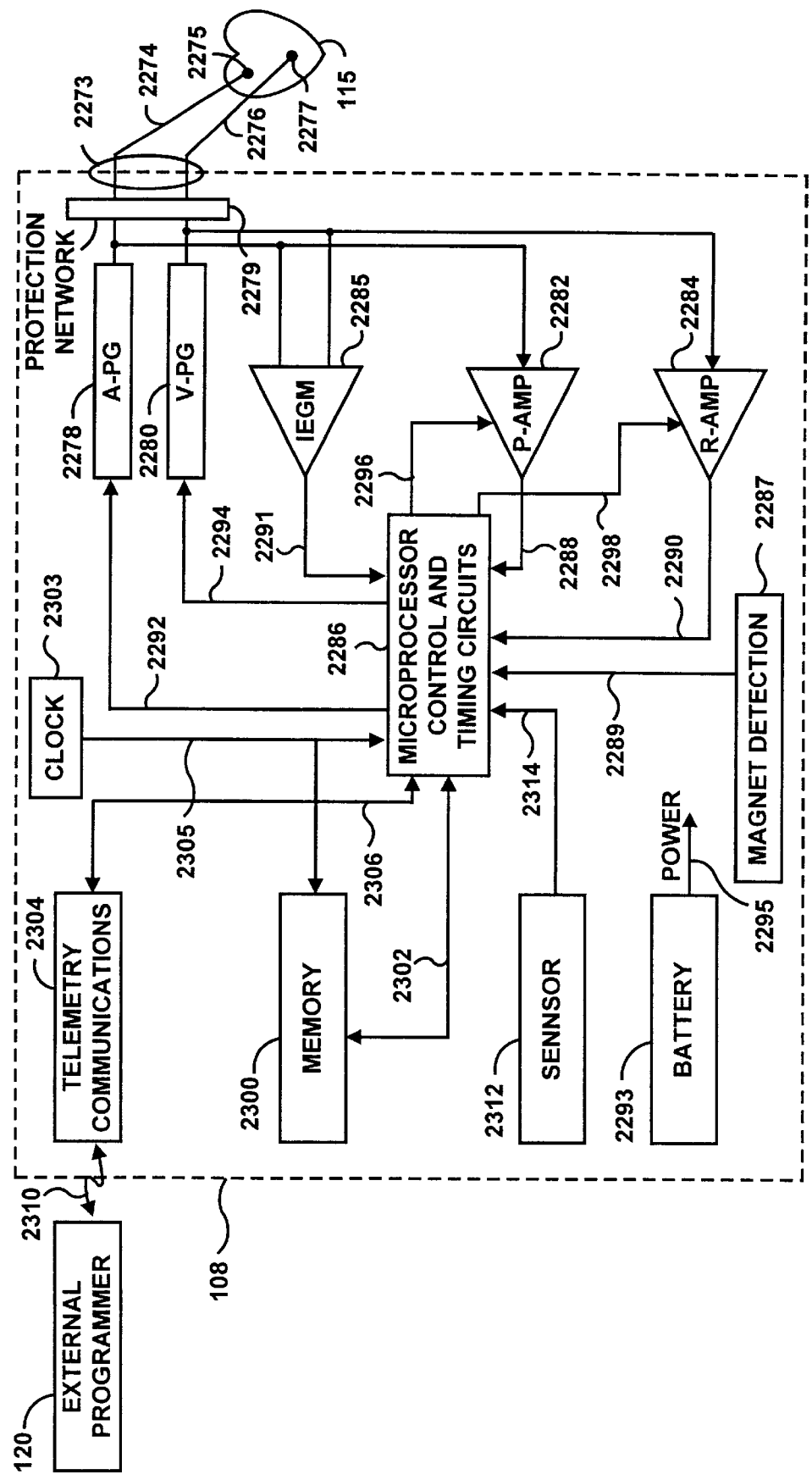
FIG. 22 shows a functional block diagram of an implantable dual-chamber pacemaker, which represents another type of implantable medical device with which the invention may be used.

FIGS. 21 and 22 represent two exemplary types of implantable stimulation devices 110, including a pacemaker configured to treat bradycardia and/or tachycardia (FIG. 22), an implantable cardioverter-defibrillator also known as ICD (FIG. 22), or a combination thereof for use with the programmer 120 of the present invention.

To better appreciate the invention, it will be helpful to have an understanding of the basic functions performed by the implantable stimulation device 110 with which the programmer 120 is used. While a dual-chamber device has been chosen for illustration purpose, it should be clear that the present invention can be used with other types. For example, the present invention could be used with a single-chamber device, that one of ordinary skill in the art could readily adapt the dual-chamber device shown in FIG. 22 to perform single-chamber functionality.

FIG. 21 shows a simplified functional block diagram of an ICD device 2120, and in FIG. 22, there is shown a simplified functional block diagram of a dual-chamber pacemaker 110 (FIG. 1). It should also be noted that in some instances the functions of an ICD and a pacemaker may be combined within the same stimulation device. However, for teaching purposes, the devices will be described as separate stimulation devices.

It is the primary function of an ICD device 2120 to sense the occurrence of an arrhythmia, and to automatically apply an appropriate electrical shock therapy to the patient's heart 115 (FIG. 1) aimed at terminating the arrhythmia. To this end, the ICD device 2120, as shown in the functional block diagram of FIG. 21, includes a control and timing circuit 2122, such as a microprocessor, state-machine or other such control circuitry, that controls a high output charge generator (or pulse generator) 2126. The high output charge generator 2126 generates electrical stimulation pulses of moderate or high energy (corresponding to cardioversion or defibrillation pulses, respectively), e.g., electrical pulses having energies of from 1 to 10 joules (moderate) or 11 to 40 joules (high), as controlled by the control/timing circuit 2122.

Such moderate or high energy pulses are applied to the patient's heart 115 through at least one lead 2130 having at least two defibrillation electrodes, such as coil electrodes 2138 and 2140. The lead 2130 preferably also includes at least one electrode for pacing and sensitivities, such as electrode 2132. Typically, the lead 2130 is transvenously inserted into the heart 115 so as to place the coil electrodes 2138 and 2140 in the apex of the heart 115 and in the superior vena cava, respectively. While only one lead 2130 is shown in FIG. 21, it is to be understood that additional defibrillation leads and electrodes may be used as desired or needed in order to efficiently and effectively apply the shock treatment generated by the high voltage generator 2126 to the patient's heart 115.

The ICD device 2120 also includes a sense amplifier (or detection circuit) 2142 that is coupled to at least one sensing electrode 2132. It is the function of the sense amplifier 2142 to sense the electrical activity of the heart 115, such as R-waves which occur upon the depolarization, and hence contraction, of ventricular tissue; and P-waves which occur upon the depolarization, and hence contraction, of atrial tissue. Thus, by sensing R-waves and/or P-waves through the sense amplifier 2142, the control/timing circuit 2122 is able to make a determination as to the rate and regularity of the patient's heart beat. Such information, in turn, allows the control/timing circuit 2122 to determine whether the heart 115 of a patient is experiencing an arrhythmia, and to apply appropriate stimulation therapy.

The control/timing circuit 2122 further has a memory circuit 2144 coupled thereto wherein the patient's historical data, and the operating parameters used by the control/timing circuit 2122 are stored. Such operating parameters define, for example, the amplitude of each shock energy pulse to be delivered to the patient's heart 115 within each tier of therapy, as well as the duration of these shock pulses. The memory 2144 may take many forms, and may be subdivided into as many different memory blocks or sections (addresses) as needed to store desired data and control information. In some embodiments, the ICD device 2120 has the ability to sense and store a relatively large amount of data as a data record, which data record may then be used to guide the operation of the device, i.e., the present operating mode of the device may be dependant, at least in part, on past performance data.

Advantageously, the operating parameters of the implantable device 2120 may be non-invasively programmed into the memory 2144 through a telemetry circuit 2146, in telecommunicative contact with the external programmer 120 by way of a suitable coupling coil 2150. The coupling coil 2150 may serve as an antenna for establishing a radio frequency (RF) communication link 2152 with the external programmer 120; or the coil 2150 may serve as a means for inductively coupling data to and from the telemetry circuit 2146 from and to the external programmer 120. Reference is made to U.S. Pat. No. 4,809,697 (Causey, III et al.) and U.S. Pat. No. 4,944,299 (Silvian) that are incorporated herein by reference. Further, such telemetry circuit 2146 advantageously allows status information relating to the operation of the ICD device 2120, as contained in the control/timing circuit 2122 or memory 2144, to be sent to the external programmer 120 through the established link 2152 or wand 122 (FIG. 5).

The control/timing circuit 2122 includes appropriate processing and logic circuits for analyzing the output of the sense amplifier 2142 and determining if such signals indicate the presence of an arrhythmia. Typically, the control/timing circuit 2122 is based on a microprocessor, or similar processing circuit, which includes the ability to process or monitor input signals (data) in a prescribed manner, e.g., as controlled by program code stored in a designated area or block of the memory 2144.

FIG. 22 shows a simplified block diagram of the circuitry needed for a dual-chamber pacemaker 110 is illustrated. The pacemaker 110 is coupled to the patient's heart 115 by way of leads 2274 and 2276, the lead 2274 having an electrode 2275 that is in contact with one of the atria of the heart 115, and the lead 2276 having an electrode 2277 that is in contact with one of the ventricles of the heart 115. The leads 2274 and 2276 are electrically and physically connected to the pacemaker 110 through a connector 2273 that forms an integral part of the housing wherein the circuits of the pacemaker 110 are housed. The connector 73 is electrically connected to a protection network 79, which network 79 electrically protects the circuits within the pacemaker 110 from excessive shocks or voltages that could appear on the electrodes 75 and/or 77 in the event such electrodes were to come in contact with a high voltage signal, e.g., from a defibrillation shock.

The leads 2274 and 2276 carry stimulating pulses to the electrodes 2275 and 2277 from an atrial pulse generator (A-PG) 2278 and a ventricular pulse generator (V-PG) 2280, respectively. Further, electrical signals from the atria are carried from the electrode 2275, through the lead 2274, to the input terminal of an atrial channel sense amplifier (P-AMP) 2282; and electrical signals from the ventricles are carried from the electrode 2277, through the lead 2276, to the input terminal of a ventricular channel sense amplifier (R-AMP) 2284. Similarly, electrical signals from both the atria and ventricles are applied to the inputs of an intracardiac electrogram (IEGM) amplifier 2285. The amplifier 2285 is typically configured to detect an evoked response from the heart 115 in response to an applied stimulus, thereby aiding in the detection of "capture". Capture occurs when an electrical stimulus applied to the heart is of sufficient energy to depolarize the cardiac tissue, thereby causing the heart muscle to contract, or in other words, causing the heart to beat. Capture does not occur when an electrical stimulus applied to the heart is of insufficient energy to depolarize the cardiac tissue.

The dual-chamber pacemaker 110 is controlled by a processor or control system 2286, which is comprised of control and timing circuitries that carry out control and timing functions. The control system 2286 receives the output signals from the atrial (P-AMP) amplifier 2282 over signal line 2288. Similarly, the control system 2286 receives the output signals from the ventricular (R-AMP) amplifier 2284 over signal line 2290, and the output signals from the IEGM amplifier 2285 over signal line 2291. These output signals are generated each time that a P-wave or an R-wave or an evoked response is sensed within the heart 115. The control system 2286 also generates trigger signals that are sent to the atrial pulse generator (A-PG) 2278 and the ventricular pulse generator (V-PG) 2280 over signal lines 2292 and 2294, respectively. These trigger signals are generated each time that a stimulation pulse is to be generated by the respective pulse generator 78 or 80. The atrial trigger signal is referred to simply as the "A-trigger", and the ventricular trigger signal is referred to as the "V-trigger".

During the time that either an A-pulse or V-pulse is being delivered to the heart 115, the corresponding amplifier, P-AMP 2282 and/or R-AMP 2284, is typically disabled by way of a blanking signal presented to these amplifiers from the control system over signal lines 2296 and 2298, respectively. This blanking action prevents the amplifiers 2282 and 2284 from becoming saturated from the relatively large stimulation pulses that are present at their input terminals during this time. This blanking action also helps prevent residual electrical signals present in the muscle tissue as a result of the pacemaker stimulation from being interpreted as P-waves or R-waves.

The pacemaker 110 further includes a memory circuit 2300 that is coupled to the control system 2286 over a suitable data/address bus 2302. This memory circuit 2300 allows certain control parameters, used by the control system 2286 in controlling the operation of the pacemaker, to be programmably stored and modified, as required, in order to customize the pacemaker's operation to suit the needs of a particular patient. Further, data sensed during the operation of the pacemaker may be stored in the memory 2300 for later retrieval and analysis.

As with the memory 2144 of the ICD device 2120 shown in FIG. 21, the memory 2300 of the pacemaker 110 (FIG. 22) may take many forms, and may be subdivided into as many different memory blocks or sections (addresses) as needed in order to allow desired data and control information to be stored.

In some embodiments, the pacemaker 110 has the ability to sense and store a relatively large amount of sensed data as a data record, which data record may then be used to guide the operation of the device. That is, the operating mode of the pacemaker 110 may be dependent, at least in part, on past performance data. For example, an average atrial rate may be determined based on the sensed atrial rate over a prescribed period of time. This average rate may then be stored and updated at regular intervals. Such stored rate may then be compared to a present atrial rate and, depending upon the difference, used to control the operating mode of the pacemaker. Other parameters, of course, in addition to (or in lieu of) atrial rate, may be similarly sensed, stored, averaged (or otherwise processed), and then used for comparison purposes against one or more currently-sensed parameters. Advantageously, modern memory devices allow for the storage of large amounts of data in this manner.

A clock circuit 2303 directs an appropriate clock signal(s) to the control system 2286, as well as to any other needed circuits throughout the pacemaker 110 (e.g., to the memory 2300 ) by way of clock bus 2305.

A telemetry/communications circuit 2304 is further included in the pacemaker 110. This telemetry circuit 2304 is connected to the control system 2286 by way of a suitable command/data bus 2306. In turn, the telemetry circuit 2304, which is included within the implantable pacemaker 110, may be selectively coupled to an external programming device or programmer 120 by means of an appropriate communication link 2310 or wand 122 (FIG. 5), which communication link 2310 may be any suitable electromagnetic link, such as an RF (radio frequency) channel, a magnetic link, an inductive link, an optical link, and the like. Advantageously, through the external programmer 120 and the communication link 2310, desired commands may be sent to the control system 2286. Similarly, through this communication link 2310 with the programmer 120, data commands (either held within the control system 2286, as in a data latch, or stored within the memory 2300) may be remotely received from the programmer 120. Similarly, data initially sensed through the leads 2274 or 2276, and processed by the microprocessor control circuits 2286, or other data measured within or by the pacemaker 110, may be stored and uploaded to the programmer 120. In this manner, non-invasive communications can be established with the implanted pacemaker 110 from a remote, non-implanted, location.

The pacemaker 110 additionally includes a battery 2293 which provides operating power to all of the circuits of the pacemaker 110 via a POWER signal line 2295.

It is noted that the pacemaker 110 in FIG. 22 is referred to as a dual-chamber pacemaker because it interfaces with both the atria and the ventricles of the heart. Those portions of the pacemaker 110 that interface with the atria, e.g., the lead 2274, the P-wave sense amplifier (or detection circuit) 2282, the A-PG 2278, and corresponding portions of the control system 2286, are commonly referred to as the "atrial channel". Similarly, those portions of the pacemaker 110 that interface with the ventricles, e.g., the lead 2276, the R-wave sense amplifier (or detection circuit) 2284, the V-pulse generator 2280, and corresponding portions of the control system 2286, are commonly referred to as the "ventricular channel".

As needed for certain applications, the pacemaker 110 may further include at least one sensor 2312 that is connected to the control system 2286 of the pacemaker 110 over a suitable connection line 2314. While this sensor 2312 is illustrated in FIG. 22 as being included within the pacemaker 110, it is to be understood that the sensor may also be external to the pacemaker 110, yet still be implanted within or carried by the patient. A common type of sensor is an activity sensor, such as a piezoelectric crystal, that is mounted to the case of the pacemaker. Other types of sensors are also known, such as sensors that sense the oxygen content of blood, respiration rate, pH of blood, body motion, and the like. The type of sensor used is not critical to the present invention. Any sensor or combination of sensors capable of sensing a physiological or physical parameter relatable to the rate at which the heart should be beating (i.e., relatable to the metabolic need of the patient), and/or relatable to whether a tachyarrhythmia is likely to soon occur, can be used. Such sensors are commonly used with "rate-responsive" pacemakers in order to adjust the rate (pacing cycle) of the pacemaker in a manner that tracks the physiological or metabolic needs of the patient.

The pacemaker 110 further includes magnet detection circuitry 2287, coupled to the control system 2286 over signal line 2289. It is the purpose of the magnet detection circuitry 2287 to detect when a magnet is placed over the pacemaker 110, which magnet may be used by a physician or other medical personnel to perform various reset functions of the pacemaker 110, and/or to signal the control system 2286 that an external programmer 120 is in place to receive data from, or send data to, the pacemaker memory 2300 or control system 2286 through the telemetry communications circuits 2304.

The control system 2286 may be realized using a variety of different techniques and/or circuits. A preferred type of control system 2286 is a microprocessor-based control system. It is noted, however, that the control system 2286 could also be realized using a state machine. Indeed, any type of control circuit or system could be employed for the control system 2286.

Representative of the types of control systems that may be used with the invention is the microprocessor-based control system described in U.S. Pat. No. 4,940,052, entitled "Microprocessor Controlled Rate-Responsive Pacemaker Having Automatic Rate Response Threshold Adjustment". Reference is also made to U.S. Pat. Nos. 4,712,555 and 4,944,298, wherein a state-machine type of operation for a pacemaker is described; and U.S. Pat. No. 4,788,980, wherein the various timing intervals used within the pacemaker and their inter-relationship are more thoroughly described. The '052, '555, '298 and '980 patents are incorporated herein by reference.

While certain preferred embodiments of the invention have been described, these embodiments have been presented by way of example only, and are not intended to limit the scope of the present invention. For example, while the various automated features have been described as being embodied within a programmer system that includes both diagnostic and device programming features, some of these features can be embodied within a purely diagnostic system.

TABLE 1

| Protocol Step (display screen) | Option #1 | Option #2 | Option #3 | Option #4 | Option #5 | Option #6 | Option #7 | Option #8 |
|---|---|---|---|---|---|---|---|---|
| Stimulation & Sensing Parameters | Skip | *View | Print | View & Print | | | | |
| Timing Parameters | Skip | *View | Print | View & Print | | | | |
| Sensor Parameters | Skip | *View | Print | View & Print | | | | |
| Battery Longevity | Skip | View | Print | *View & Print | | | | |
| Battery Voltage & Impedance | Skip | View | Print | *View & Print | | | | |

TABLE 1-continued

| Protocol Step (display screen) | Option #1 | Option #2 | Option #3 | Option #4 | Option #5 | Option #6 | Option #7 | Option #8 |
|---|---|---|---|---|---|---|---|---|
| Battery Current | Skip | View | Print | *View & Print | | | | |
| Slaved NIPS | Skip | *Test & Print | | | | | | |
| NIPS | Skip | *Test & Print | | | | | | |
| Quick Check | Skip | View | Print | *View & Print | | | | |
| Event Histogram | Skip | *View | Print | View & Print | Clear | View & Clear | Print & Clear | View, Print & Clear |
| Heart Rate Histogram | Skip | *View | Print | View & Print | Clear | View & Clear | Print & Clear | View, Print & Clear |
| Atrial Rate Histogram | Skip | *View | Print | View & Print | Clear | View & Clear | Print & Clear | View, Print & Clear |
| R wave Histogram | Skip | View | Print | *View & Print | Clear | View & Clear | Print & Clear | View, Print & Clear |
| P wave Histogram | Skip | View | Print | *View & Print | Clear | View & Clear | Print & Clear | View, Print & Clear |
| Sensor Histogram | Skip | View | Print | *View & Print | Clear | View & Clear | Print & Clear | View, Print & Clear |
| ER Polarization Test | Skip | *Test & Print | | | | | | |
| ER Test | Skip | *Test & Print | | | | | | |
| Vent Capture Test | Skip | *Test & Print | | | | | | |
| Atrial Capture Test | Skip | *Test & Print | | | | | | |
| Vent Sense Test | Skip | *Test & Print | | | | | | |
| Atrial Sense Test | Skip | *Test & Print | | | | | | |
| Strength Duration Test | Skip | *Test & Print | | | | | | |
| Retrograde Conduction Test | Skip | *Test & Print | | | | | | |
| Long Term Threshold Record | Skip | View | Print | *View & Print | | | | |
| 7-Day Threshold Record | Skip | View | Print | *View & Print | | | | |
| Loss Of Capture Log | Skip | View | Print | *View & Print | | | | |
| Threshold Histogram | Skip | View | Print | *View & Print | | | | |
| Stimulation Histogram | Skip | View | Print | *View & Print | | | | |
| Threshold Search Difference Histogram | Skip | View | Print | *View & Print | | | | |
| Atrial Lead Measurements | Skip | View | Print | *View & Print | | | | |
| Auto Set | Skip | *Test & Print | | | | | | |
| Rate Prediction | Skip | *Test & Print | | | | | | |
| Auto Mode Switch Log | Skip | View | Print | *View & Print | | | | |
| Rhythm Log 12345X | Skip | *View | Print | View & Print | | | | |
| Event Record | Skip | View | Print | *View & Print | | | | |

TABLE 1-continued

| Protocol Step (display screen) | Option #1 | Option #2 | Option #3 | Option #4 | Option #5 | Option #6 | Option #7 | Option #8 |
|---|---|---|---|---|---|---|---|---|
| Event Snapshots | Skip | *View | Print | View & Print | | | | |
| IEGM Snapshots | Skip | View | Print | *View & Print | | | | |
| Event Bar Graph | Skip | View | Print | *View & Print | | | | |
| Rate Bar Graph | Skip | View | Print | *View & Print | | | | |
| Sensor Bar Graph | Skip | View | Print | *View & Print | | | | |
| AV Delay Bar Graph | Skip | View | Print | *View & Print | | | | |
| Patient Data | Skip | View | Print | *View & Print | | | | |
| Clear All Diagnostics Data | Skip | View | Print | *View & Print | | | | |
| Send Data To Database | Skip | *View | | | | | | |
| Final Summary | Skip | View | Print | *View & Print | | | | |
| End Session | Skip | *View | | | | | | |

What is claimed is:

1. In a dual-chamber implantable stimulation device, a method of determining atrial capture threshold while avoiding pacemaker mediated tachycardias, the method comprising the steps of:

generating atrial and ventricular stimulation pulses while maintaining ventricular pulse amplitude at a level known to ensure capture in the ventricle;

automatically lengthening the AV Delay;

detecting capture based on the absence or presence of a P-wave with each atrial stimulation pulse corresponding to loss-of-capture or cardiac contraction, respectively;

adjusting atrial stimulation pulse amplitude until a loss of capture occurs; and in response to a loss of capture, delivering a backup atrial stimulation pulse concurrent with the ventricular stimulation pulse.

2. The method, as recited in claim 1, further comprising the step of:

programmably lengthening the post-ventricular refractory period (PVARP) to further reduce the possibility of premature and retrograde P-waves being detected as true cardiac contractions.

3. A dual-chamber implantable stimulation device having means for determining atrial capture threshold while avoiding pacemaker mediated tachycardias, the device comprising:

a pulse generator configured to generate atrial and ventricular stimulation pulses to a patient's heart;

detection circuitry, coupled to the pulse generator, configured to detect the absence or presence of P-waves with each atrial stimulation pulse corresponding to loss-of-capture or cardiac contraction, respectively; and a processor, coupled to the pulse generator and the detection circuitry, programmed to automatically lengthen the AV Delay prior to triggering the pulse generator to initiate an atrial capture threshold test and, in response to a loss of capture, to restore the atrial stimulation pulse amplitude to a value above capture threshold, and further programmed to trigger the pulse generator to deliver a backup atrial stimulation pulse concurrent with the ventricular stimulation pulse.

4. The device, as recited in claim 3, wherein:

the device further comprises timing circuitry, coupled to the processor, configured to control a plurality of intervals including a post-ventricular refractory period (PVARP); and the processor is further programmed to automatically lengthen the post-ventricular refractory period (PVARP) during the capture threshold test such that the possibility of premature and retrograde P-waves being detected as true cardiac contractions is reduced.

5. The device, as recited in claim 4, wherein:

the processor is further programmed to automatically restore the post ventricular refractory period (PVARP) subsequent to the capture threshold test.

6. A dual-chamber implantable stimulation device having means for determining atrial capture threshold while avoiding pacemaker mediated tachycardias, the device comprising:

pulse generating means for generating atrial and ventricular stimulation pulses to a patient's heart;

detecting means for detecting the absence or presence of P-waves with each atrial stimulation pulse corresponding to loss-of-capture or cardiac contraction, respectively; and control means, coupled to the pulse generating means and the detecting means, for automatically lengthening the AV Delay prior to triggering the pulse generating means to initiate an atrial capture threshold test and, in response to a loss of capture, for triggering the pulse generating means to deliver a backup atrial stimulation pulse concurrent with a ventricular stimulation pulse.

7. The device, as recited in claim 6, wherein:

the device further comprises timing means for controlling a plurality of intervals including a post-ventricular refractory period (PVARP); and the control means includes means for automatically lengthening the post-ventricular refractory period (PVARP) during the capture threshold test such that the possibility of premature and retrograde P-waves being detected as true cardiac contractions is reduced.

8. The device, as recited in claim 6, wherein:

the control means includes means for automatically restoring the post ventricular refractory period (PVARP) subsequent to the capture threshold test value.

* * * * *